(12) United States Patent
Thomas-Tikhonenko et al.

(10) Patent No.: US 10,983,109 B2
(45) Date of Patent: Apr. 20, 2021

(54) COMPOSITIONS AND METHODS FOR TREATING B-LYMPHOID MALIGNANCIES

(71) Applicants: The Children's Hospital of Philadelphia, Philadelphia, PA (US); The Trustees of the University of Pennsylvania, Philadelphia, PA (US)

(72) Inventors: Andrei Thomas-Tikhonenko, Philadelphia, PA (US); Elaine Chung, Philadelphia, PA (US); James Psathas, Trappe, PA (US)

(73) Assignee: THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 0 days.

(21) Appl. No.: 14/397,060

(22) PCT Filed: May 1, 2013

(86) PCT No.: PCT/US2013/039067
§ 371 (c)(1),
(2) Date: Oct. 24, 2014

(87) PCT Pub. No.: WO2013/166150
PCT Pub. Date: Nov. 7, 2013

(65) Prior Publication Data
US 2015/0110804 A1    Apr. 23, 2015

Related U.S. Application Data

(60) Provisional application No. 61/640,987, filed on May 1, 2013.

(51) Int. Cl.
| | |
|---|---|
| *G01N 33/53* | (2006.01) |
| *G01N 33/50* | (2006.01) |
| *C12Q 1/48* | (2006.01) |
| *C07K 16/00* | (2006.01) |
| *G01N 33/573* | (2006.01) |
| *A61K 38/00* | (2006.01) |

(52) U.S. Cl.
CPC ......... *G01N 33/5011* (2013.01); *C12Q 1/485* (2013.01); *G01N 33/5052* (2013.01); *A61K 38/00* (2013.01); *G01N 33/573* (2013.01); *G01N 2333/70596* (2013.01); *G01N 2333/91215* (2013.01); *G01N 2500/02* (2013.01); *G01N 2500/10* (2013.01)

(58) Field of Classification Search
None
See application file for complete search history.

(56) References Cited

U.S. PATENT DOCUMENTS 8,637,032 B2 * 1/2014 Long et al. ............... 424/153.1
2012/0082664 A1   4/2012 Bernett et al.

FOREIGN PATENT DOCUMENTS

| WO | 2008/033746 A2 | 3/2008 |
|---|---|---|
| WO | 2012/054748 A2 | 4/2012 |

OTHER PUBLICATIONS

Nutt et al., Identification of BSAP (Pax-5) target genes in early B-cell development by loss- and gain-of-function experiments, EMBO J., 1998, 2319-33, 17(8).
Kozmik et al., The promoter of the CD19 gene is a target for the B-cell-specific transcription factor BSAP, Mol Cell Biol., 1992, 2662-72, 12(6).
Tedder et al., CD19: A promising B cell target for rheumatoid arthritis, Nat. Rev. Rheumatol., 2009, 572-577, 5.
Scheuermann et al., CD19 antigen in leukemia and lymphoma diagnosis and immunotherapy, Leuk Lymphoma, 1995, 385-397, 18.
Davies et al., Combining CD19 Redirection and Alloanergization to Generate Tumor-Specific Human T Cells for Allogeneic Cell Therapy of B-Cell Malignancies, Cancer Res., 2010, 3915-3924, 70.
Awan et al., CD19 targeting of chronic lymphocytic leukemia with a novel Fc-domain-engineered monoclonal antibody, Blood., 2010, 1204-13, 115(6).
Sapra et al., Improved outcome when B-cell lymphoma is treated with combinations of immunoliposomal anticancer drugs targeted to both the CD19 and CD20 epitope, Clin Cancer Res., 2004, 2530-7, 10(7).
Brooks et al., Binding of Cytoplasmic Proteins to the CD19 Intracellular Domain Is High Affinity, Competitive, and Multimeric, J. Immunol., 2004, 7556-7564,172.
Chen et al., The 3BP2 Adapter Protein Is Required for Optimal B-Cell Activation and Thymus-Independent Type 2 Humoral Response, Mol. Cell Biol., 2007, 3109-3122, 27.
Fujimoto et al., CD19 regulates Src family protein tyrosine kinase activation in B lymphocytes through processive amplification, Immunity., 2000, 47-57, 13(1).
O'Rourke et al., CD19 as a membrane-anchored adaptor protein of B lymphocytes: costimulation of lipid and protein kinases by recruitment of Vav, Immunity.,1998, 635-45, 8(5).
Tuveson et al., CD19 of B cells as a surrogate kinase insert region to bind phosphatidylinositol 3-kinase, Science, 1993, 986-9, 260(5110).
Uckun et al., Recombinant human CD19-ligand protein as a potent antileukaemic agent, Br. J. Haematol., 1999, 15-23, 153.
Buhl et al., Phosphorylation of CD19 Y484 and Y515, and Linked Activation of Phosphatidylinositol 3-Kinase, Are Required for B Cell Antigen Receptor-Mediated Activation of Bruton's Tyrosine Kinase, J. Immunol., 1999, 4438-4446, 162.
Otero et al., Cd19-dependent activation of Akt kinase in B-lymphocytes, J. Biol. Chem., 2001, 1474-1478, 276.

(Continued)

*Primary Examiner* — Chun W Dahle
(74) *Attorney, Agent, or Firm* — Robert C. Netter Jr.; Dann, Dorfman, Herrell & Skillman

(57) ABSTRACT

Compositions and methods for inhibiting, treating, and/or preventing a B-cell neoplasm are provided.

Figure 1:
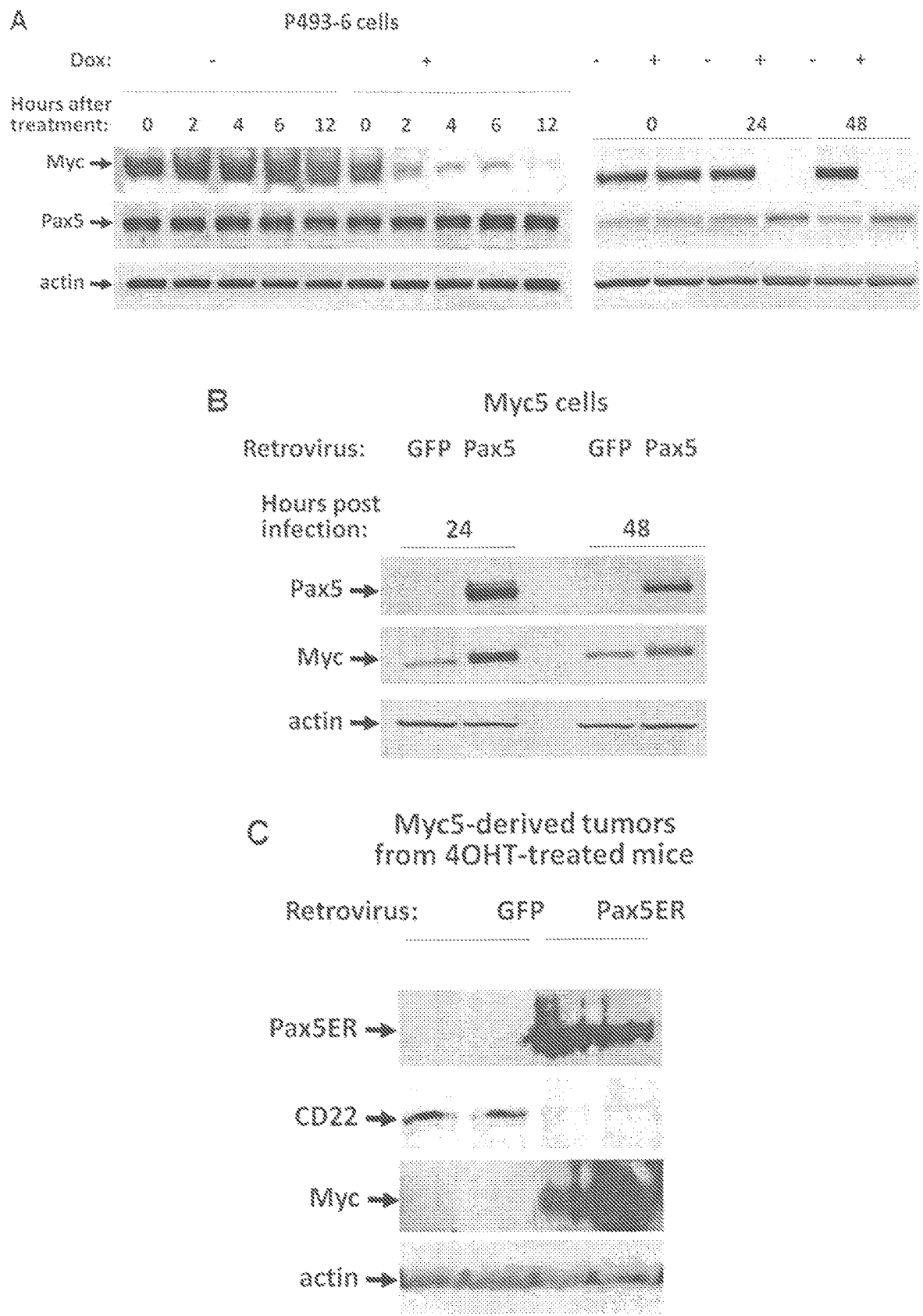
Figure 1:
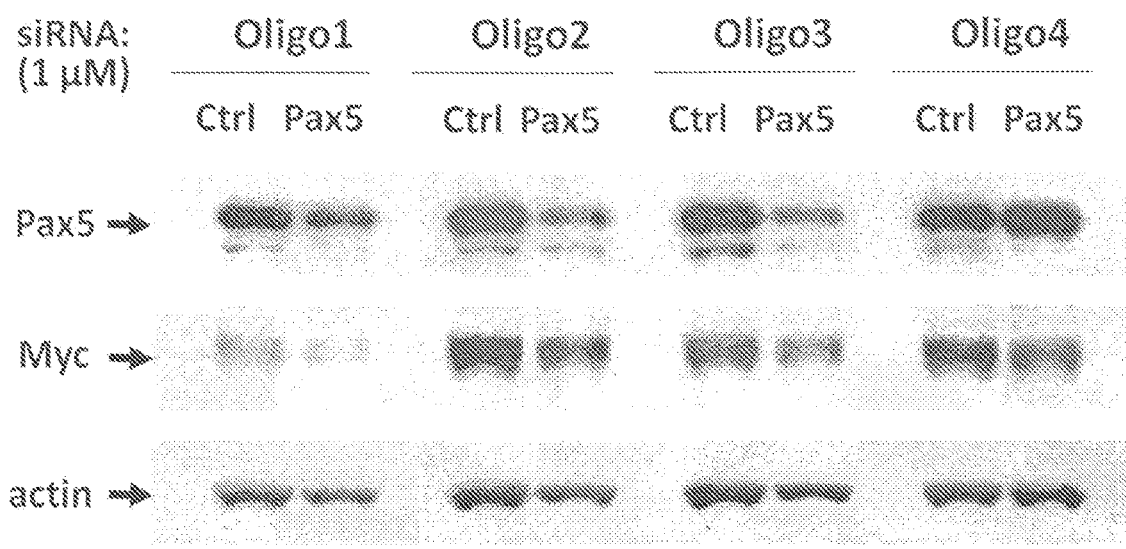
Figure 1:
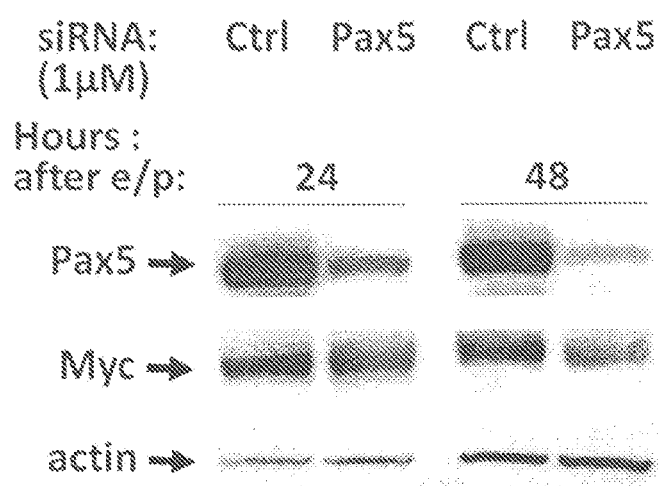

11 Claims, 31 Drawing Sheets
Specification includes a Sequence Listing.

(56) References Cited

OTHER PUBLICATIONS

Fujimoto et al., Complementary Roles for CD19 and Bruton's Tyrosine Kinase in B Lymphocyte Signal Transduction, J. Immunol., 2002, 5465-5476, 168.
Aiba et al., Regulation of B-cell development by BCAP and CD19 through their binding to phosphoinositide 3-kinase, Blood, 2008, 1497-1503,111.
Gold et al., Targets of B-cell antigen receptor signaling: the phosphatidylinositol 3-kinase/Akt/glycogen synthase kinase-3 signaling pathway and the Rap1 GTPase, Immunol Rev., 2000, 47-68, 176.
Lannutti et al., CAL-101, a p110delta selective phosphatidylinositol-3-kinase inhibitor for the treatment of B-cell malignancies, inhibits PI3K signaling and cellular viability, Blood, 2011, 591-4, 117(2).
Engel, et al., "Abnormal B Lymphocyte Delevopment, Activation, and Differentiation in Mice that Lack or Overexpress the CD19 Signal Transduction Molecule", Immunity (1995) 3:39-50.
Ishiura, N., et al. "Differential Phosphorylation of Functional Tyrosines in CD19 Modulates B-Lymphocyte Activation" Eur. J. Immunol. (2010) 40:1192-1204.
Beckwith, M., et al. "The Protein Product of the Proto-oncogene c-cbl Forms a Complex with Phosphatidylinositol 3-Kinase p85 and CD19 in Anti-IgM-Stimulated Human B-Lymphoma Cells" Blood (1996) 88:3502-3507.
Chung, E.Y., et al. "CD19 is a B Cell Receptor-independent Actoivator of MYC-driven B-lymphomagenesis" J. Clin. Invest., (May 1, 2012) 122:2257-2266.
So, et al., "PI3K Signaling in B and T Lymphocytes: New Developments and Therapeutic Advances", Biochem. J. (2012) 442(3):465-481.
Wang, Y., et al., "The physiologic role of CD19 cytoplasmic tyrosines", Immunity (2002) 17(4):501-14.
Luo, J., et al., "Targeting the PI3K-Akt pathway in human cancer: Rationale and promise" Cancer Cell (2003) 4:257-262.
Poe, J.C., et al., "A c-Myc and Surface CD19 Signaling Amplification Loop Promotes B Cell Lymphoma Development and Progression in Mice" J. Immunology (2012) 189: 2318-2325.
Wang, K., et al., "CD19: a biomarker for B cell development, lymphoma diagnosis and therapy" Experimental Hematology & Oncology (2012) 1:36.

* cited by examiner

D

E

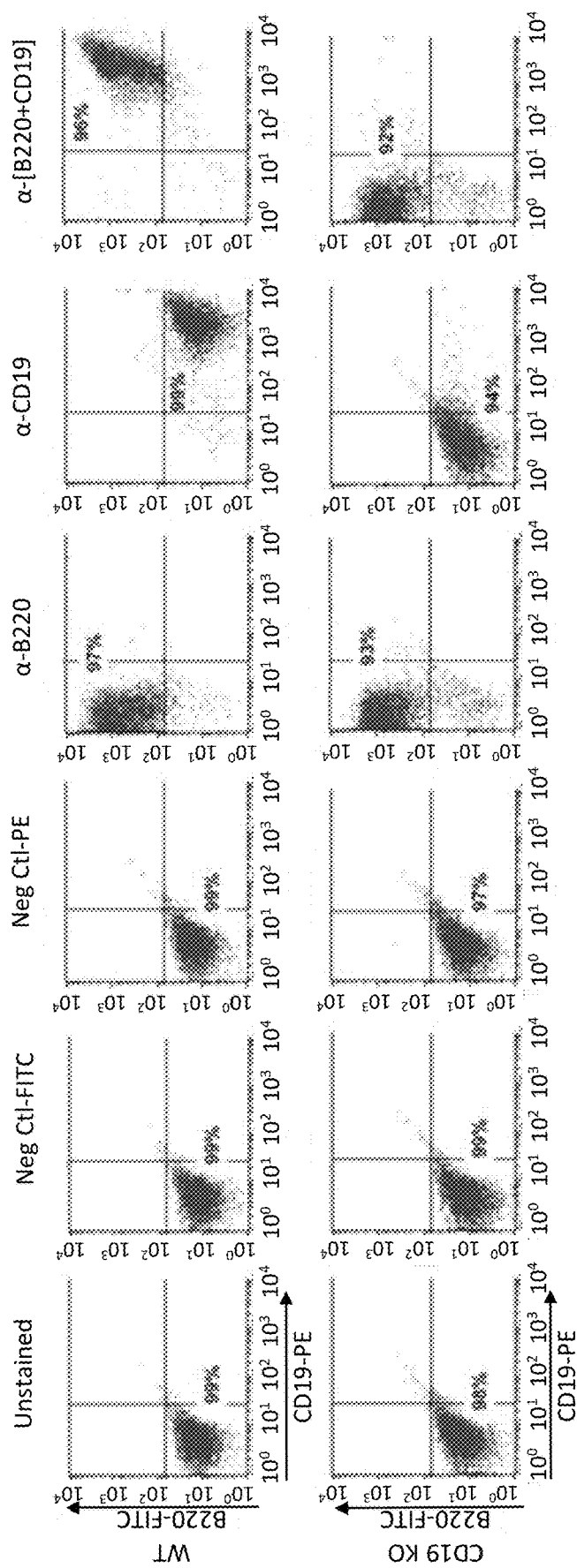
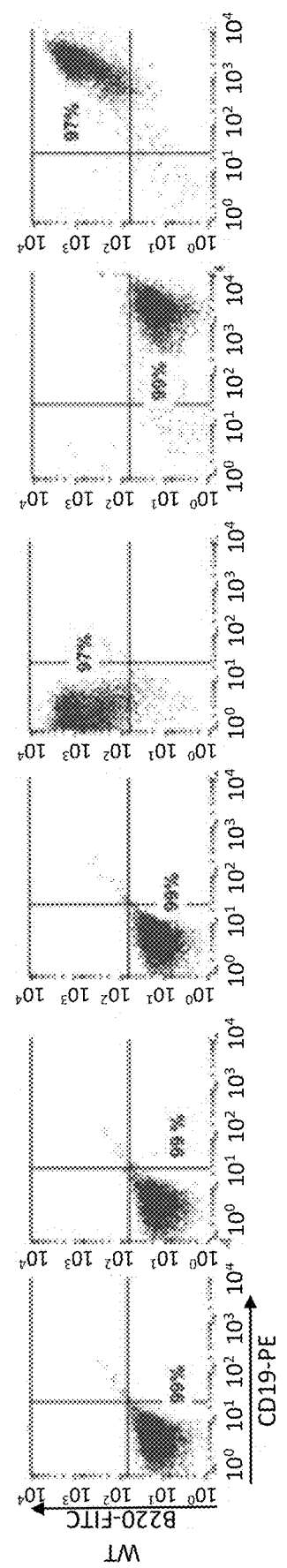
Figure 4A
Figure 4B

F

G

A

B

SEQUENCE LISTING

<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: CDK4 sense primer

<400> SEQUENCE: 1
caatgttgta cggctgatgg                                        20

<210> SEQ ID NO 2
<211> LENGTH: 20
<212> TYPE: DNA
<213> ORGANISM: Artificial Sequence
<220> FEATURE:
<223> OTHER INFORMATION: CDK4 antisense primer

<400> SEQUENCE: 2

```
caggccgctt agaaactgac                                                20

<210> SEQ ID NO 3
<211> LENGTH: 20
<212> TYPE: DNA
<213> ORGANISM: Artificial Sequence
<220> FEATURE:
<223> OTHER INFORMATION: ODC1 sense primer

<400> SEQUENCE: 3
gtggcaactc atgaagcaga                                                20

<210> SEQ ID NO 4
<211> LENGTH: 20
<212> TYPE: DNA
<213> ORGANISM: Artificial Sequence
<220> FEATURE:
<223> OTHER INFORMATION: ODC1 antisense primer

<400> SEQUENCE: 4
tgcaggcaag agctacaaga                                                20

<210> SEQ ID NO 5
<211> LENGTH: 20
<212> TYPE: DNA
<213> ORGANISM: Artificial Sequence
<220> FEATURE:
<223> OTHER INFORMATION: LDHA sense primer

<400> SEQUENCE: 5
tccgttacct gatgggagag                                                20

<210> SEQ ID NO 6
<211> LENGTH: 20
<212> TYPE: DNA
<213> ORGANISM: Artificial Sequence
<220> FEATURE:
<223> OTHER INFORMATION: LDHA antisense primer

<400> SEQUENCE: 6
gtaggcactg tccaccacct                                                20

<210> SEQ ID NO 7
<211> LENGTH: 16
<212> TYPE: PRT
<213> ORGANISM: Artificial Sequence
<220> FEATURE:
<223> OTHER INFORMATION: ITAM motif
<220> FEATURE:
<221> NAME/KEY: VARIANT
<222> LOCATION: 4, 16
<223> OTHER INFORMATION: Xaa = Leu or Ile
<220> FEATURE:
<221> NAME/KEY: VARIANT
<222> LOCATION: 2, 3, 5-10, 14, 15
<223> OTHER INFORMATION: Xaa = any amino acid
<220> FEATURE:
<221> NAME/KEY: VARIANT
<222> LOCATION: 11, 12
<223> OTHER INFORMATION: Xaa = any amino acid or absent

<400> SEQUENCE: 7

Tyr Xaa Xaa Xaa Xaa Xaa Xaa Xaa Xaa Xaa Xaa Xaa Tyr Xaa Xaa Xaa
1               5                   10                  15
```

COMPOSITIONS AND METHODS FOR TREATING B-LYMPHOID MALIGNANCIES

This application is a § 371 application of PCT/US2013/039067, filed May 1, 2013, which claims priority under 35 U.S.C. § 119(e) to U.S. Provisional Patent Application No. 61/640,987, filed on May 1, 2012. The foregoing applications are incorporated by reference herein.

This invention was made with government support under Grant Nos. R01 CA102709, T32 HL007439, and T32 CA115299 awarded by the National Institutes of Health. The Government has certain rights in this invention.

FIELD OF THE INVENTION

The present invention relates to the field of cancer therapy. Specifically, compositions and methods for inhibiting, treating, and/or preventing cancer are disclosed.

BACKGROUND OF THE INVENTION

Several publications and patent documents are cited throughout the specification in order to describe the state of the art to which this invention pertains. Each of these citations is incorporated herein by reference as though set forth in full.

The concept of oncogene addiction is particularly well-validated in hematological malignancies (Felsher, D. W. (2003) Nat. Rev. Cancer 3:375-380). "Liquid" tumors are thought to depend on fewer genetic alterations and thus be more sensitive to drugs targeting abnormally expressed oncoproteins, Gleevec vs. Bcr-Abl being the prime example (Rowley, J. D. (2001) Nat. Rev. Cancer 1:245-250; Druker, B. J. (2002) Cancer Cell 1:31-36). Additionally, initiating oncogenes in many lymphomas and leukemias are easily identified as products of recurrent chromosomal translocations. For example, in human Burkitt's (BL) and some diffuse large B-cell (DLBLC) lymphomas, the t(8;14) translocation places c-Myc under the control of the immunoglobulin heavy chain (IgH) gene enhancer (Taub et al. (1982) Proc. Natl. Acad. Sci., 79:7837-7841; Dalla-Favera et al. (1982) Proc. Natl. Acad. Sci., 79:7824-7827). A similar translocation has been identified in murine plasmacytomas (Shen-Ong et al. (1982) Cell 31:443-452).

Another protein implicated in B-cell neoplasms is paired box transcription factor 5, or Pax5. Pax5 controls B-cell differentiation from the pro-B to the mature B cell stage and is chiefly responsible for expression of the B-cell receptor (BCR) complex (Busslinger, M. (2004) Annu. Rev. Immunol., 22:55-79; Monroe, J. G. (2006) Nat. Rev. Immunol., 6:283-294). This is achieved via direct transcriptional activation of genes encoding CD79a (a.k.a. Ig-α; Maier et al. (2003) Nucleic Acids Res., 31:5483-5489), which heterodimerizes on the cell surface with Ig-13 (Schamel et al. (2000) Immunity 13:5-14), and the CD19 co-receptor (Nutt et al. (1998) EMBO J., 17:2319-2333; Kozmik et al. (1992) Mol. Cell Biol., 12:2662-2672). PAX5 is also overexpressed through chromosomal translocations in a subset of B cell lymphomas. The Pax5 gene is affected by a relatively rare but persistent t(9; 14)(p13; q32) translocation associated with aggressive B cell non-Hodgkin lymphomas (NHL) (Offit et al. (1992) Blood 80:2594-2599; Cook et al. (2004) Hum. Pathol., 35:447-454; Busslinger et al. (1996) Proc. Natl. Acad. Sci., 93:6129-6134; Iida et al. (1996) Blood 88:4110-4117; Morrison et al. (1998) Blood 92:3865-3878; Poppe et al. (2005) Genes Chromosomes Cancer 44:218-223). In addition to genomic rearrangements, the Pax5 gene is also affected by somatic hypermutations, in particular in diffuse large B-cell lymphoma (DLBCL) patients (Pasqualucci et al. (2001) Nature 412:341-346). There are several other recurrent translocations [e.g., t(7;9)(q11;p13) and t(9; 12)(q11;p13)] involving Pax5, which were found in B-cell acute lymphocytic leukemia (B-ALL). These translocations result in the fusion of the Pax5 and ELN and ETV6/TEL genes and are regarded as dominant-negative inhibitors of Pax5 transcriptional activity (Bousquet et al. (2007) Blood 109:3417-3423; Cazzaniga et al. (2001) Cancer Res., 61:4666-4670). Furthermore, the genome-wide analysis of B-ALL using high-resolution SNP arrays and direct genome sequencing yielded several loss of function mutations in Pax5 (Mullighan et al. (2007) Nature 446:758-764). However, the effect of PAX5 on other oncogenic transcription factor-controlled pathways is unknown.

SUMMARY OF THE INVENTION

In accordance with the present invention, methods of inhibiting, treating, and/or preventing cancer in a subject are provided. In certain embodiments, the methods comprise administering to the subject a therapeutically effective amount of at least one inhibitor of the CD19-PI3K interaction. In a particular embodiment, the method further comprises the administration of at least one other anti-cancer measure, such as the administration of at least one other chemotherapeutic agent and/or administration of radiation therapy.

In accordance with another aspect of the instant invention, methods of screening for chemotherapeutic agents (e.g., inhibitors of the CD19-PI3K interaction) are also provided. In a particular embodiment, the methods comprise performing a binding assay in the presence of at least one test compound and comparing the amount of CD19-PI3K binding to the amount of binding in the absence of the test compound, wherein a decrease in the binding indicates that the test compound is an inhibitor.

In accordance with the instant invention, methods of determining whether a cancer is sensitive or resistant to an inhibitor of the CD19-PI3K interaction are provided.

BRIEF DESCRIPTIONS OF THE DRAWING

FIG. 1 demonstrates that Pax5 regulates c-Myc protein levels. All panels represent immunoblotting analyses of proteins indicated on the left. Actin was used as a loading control. FIG. 1A shows P493-6 cells either untreated (0 hour) or treated with Dox for indicated intervals prior to harvesting. FIG. 1B shows Myc5 cells infected with either the empty MIGR1 vector ("GFP") or Pax5-MIGR1 ("Pax5"). Protein lysates were prepared 24 and 48 hours post infection. FIG. 1C shows protein lysates obtained from Myc tumors samples. Prior to implantation, Myc5 cells were infected with either the empty MIGR1 vector ("GFP") or Pax5ERMIGR1 ("Pax5ER"). FIG. 1D shows P493-6 cells electroporated using various anti-Pax5 ("Pax5") or control ("Ctrl") siRNAs. FIG. 1E shows P493-6 cells that were electroporated with 1 µM of either control or anti-Pax5 siRNA. Lysates were harvested 24 and 48 hours post electroporation.

Figure 2:
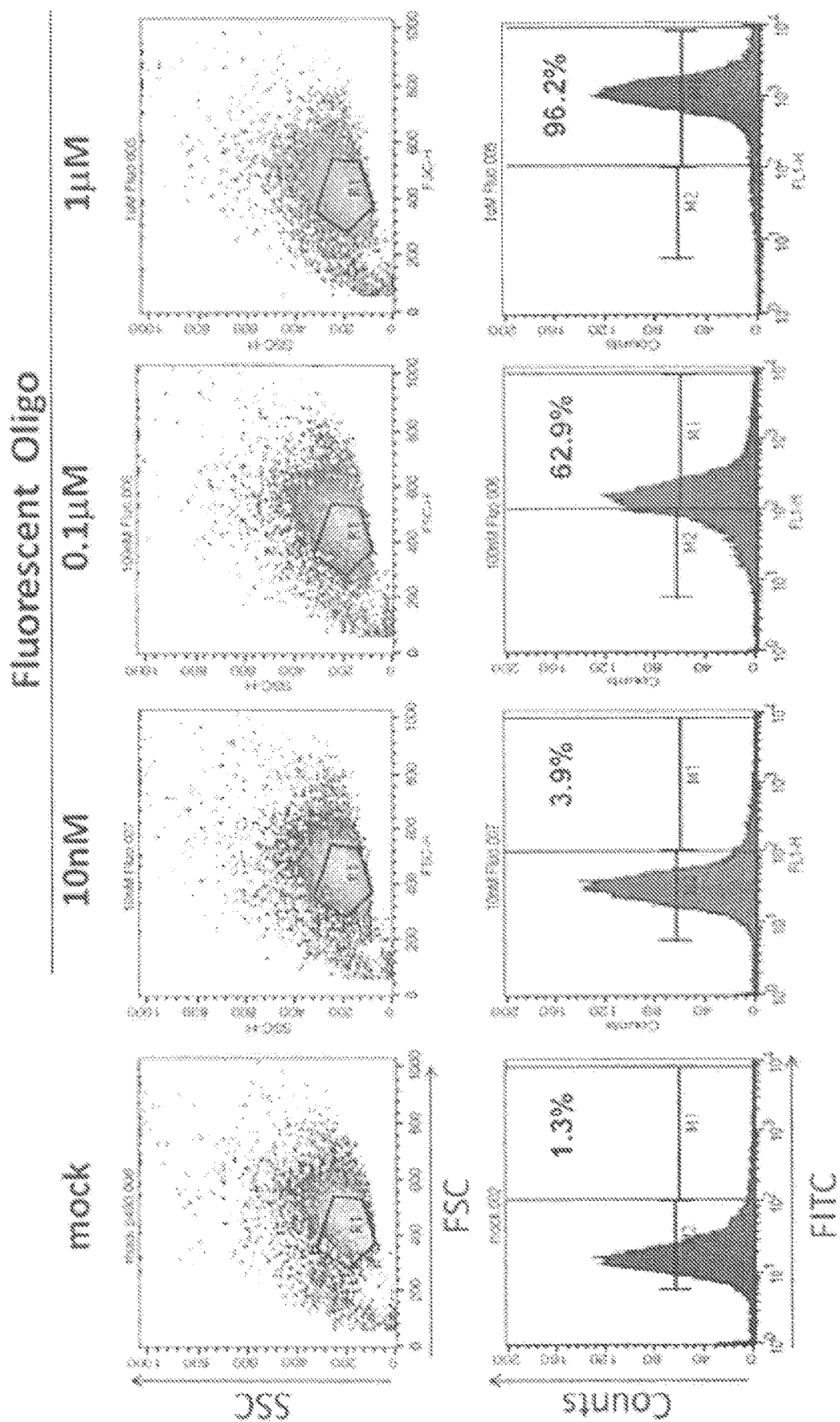

FIG. 2 shows the efficiency of RNA electroporation into P493-6 cells. P493-6 cells were electroporated with 10 nM, 0.1 µM or 1 µM of BLOCK-IT® FITC-labeled, double-stranded RNA oligos by Amaxa®. Flow cytometry was performed 24 hours after electroporation to determine the percentage of FITC-positive cells.

Figure 3:
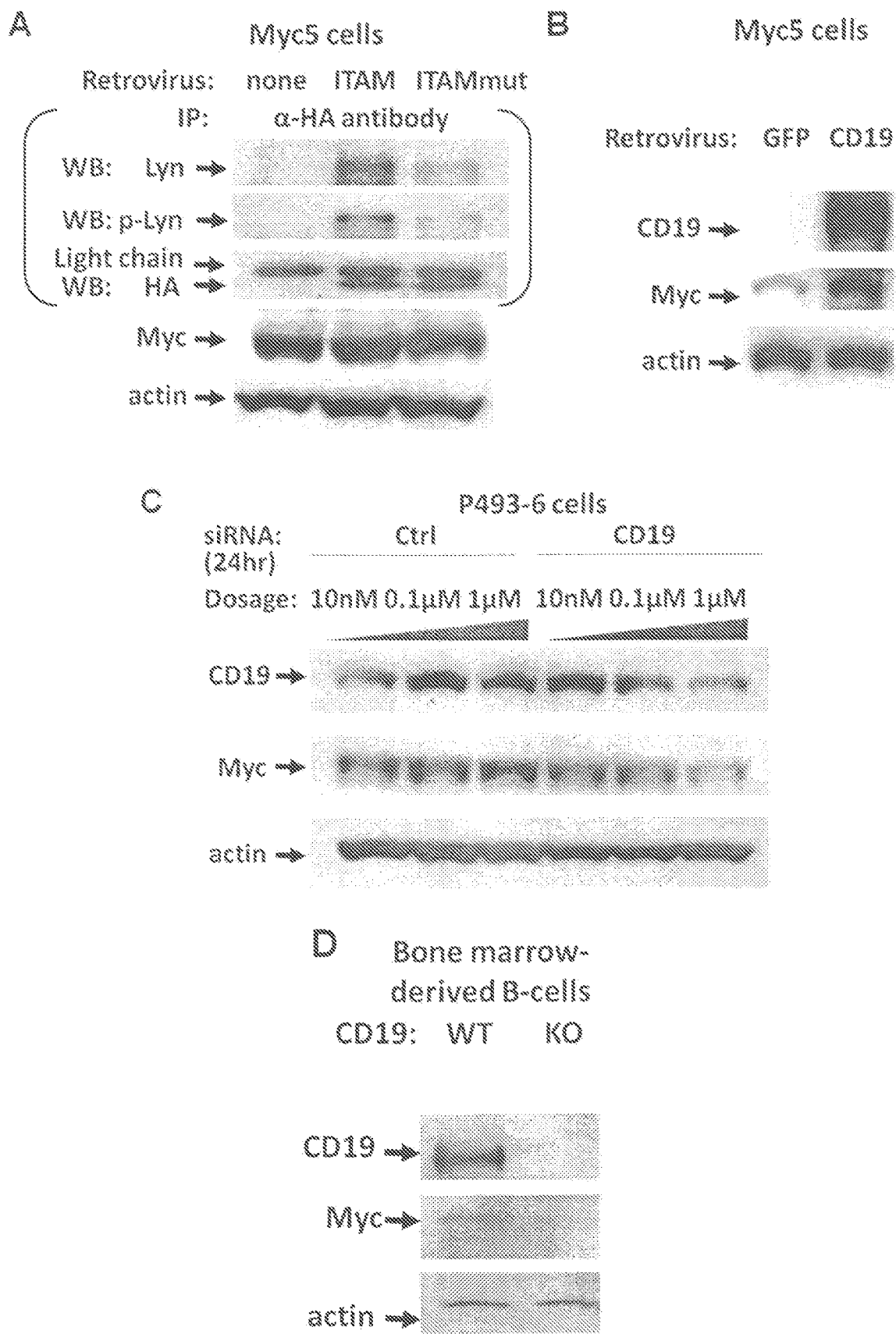
Figure 3:
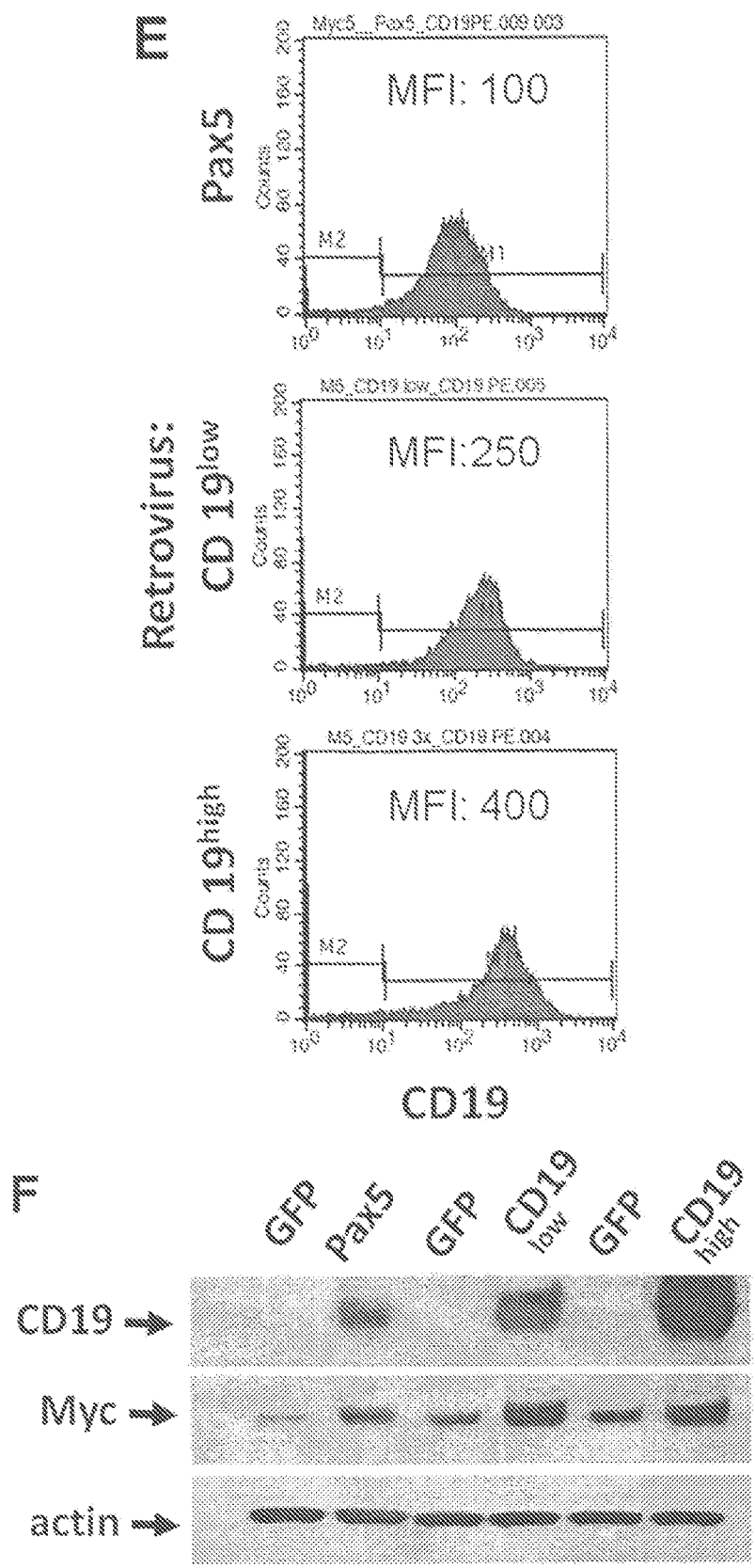
Figure 3:
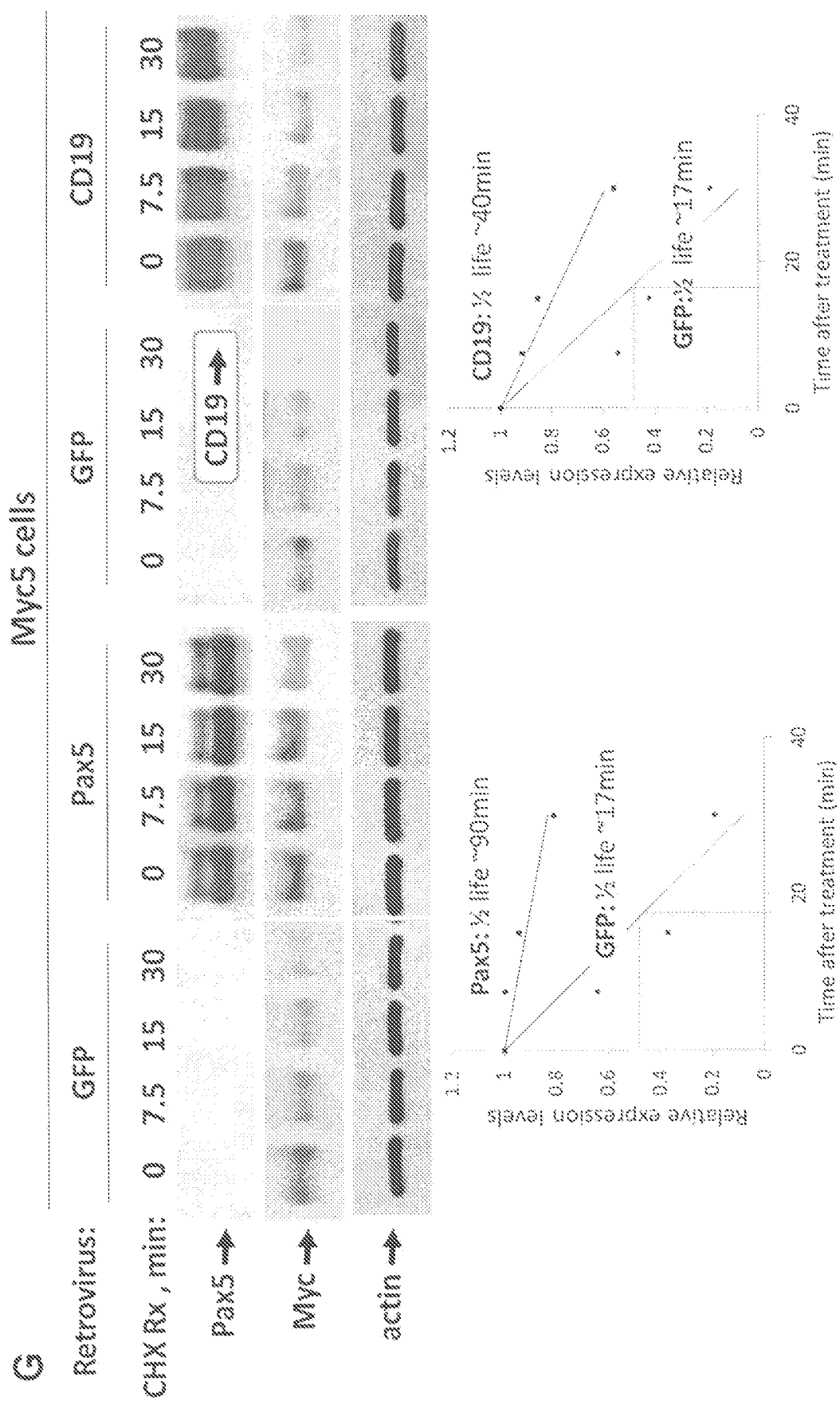
Figure 3:
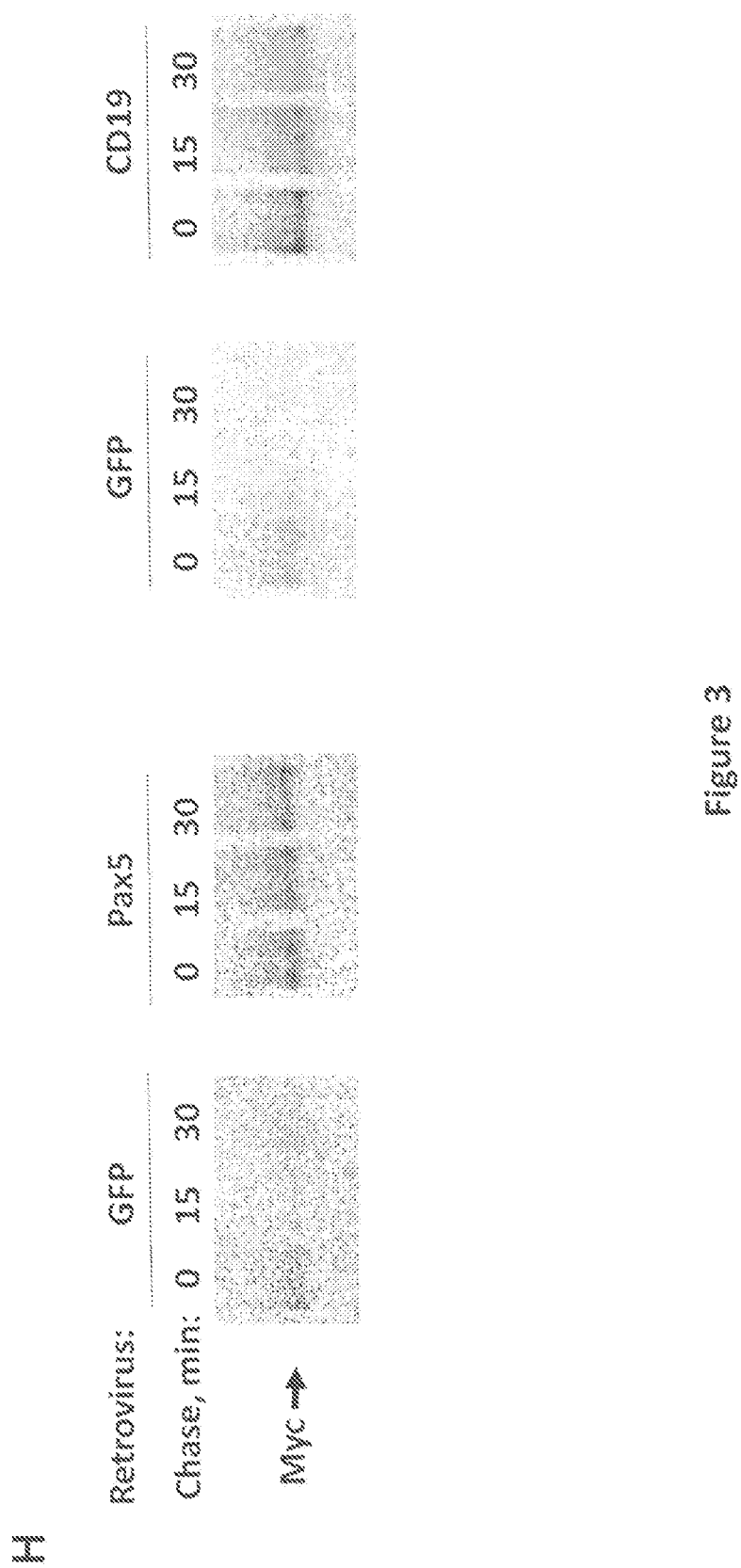

FIG. 3 shows that Pax5 regulates c-Myc protein levels through CD19. All figures except FIGS. 3E and 3H represent immunoblotting analyses of proteins indicated on the left. Actin was used as a loading control. In bracketed panels of FIG. 3A, whole cell lysates from Myc5 cells expressing HA-tagged wild-type or mutant ("mut") ITAM were subjected to immune-precipitation with an α-HA antibody followed by immunoblotting with antibody against total Lyn, Tyr396-phospho-Lyn, or another α-HA antibody. In the bottom panels, lysates from the same cells were immunoblotted with antibodies against c-Myc, and β-actin. FIG. 3B shows CD19 and Myc levels in Myc5 cells transduced with either empty ("GFP") or the CD19-encoding retrovirus ("CD19"). FIG. 3C shows Pax5, CD19 and Myc levels in P493-6 cells electroporated with increasing concentrations of either control or α-CD19 siRNA. FIG. 3D shows CD19 and Myc levels in bone marrow-derived B-cells from wild-type ("WT") and CD19-null ("KO") mice. FIG. 3E shows flow cytometric detection of CD19 expression on the surface of Myc5 cells expressing either Pax5 or low/high levels of CD19. Mean fluorescent intensities (MFI) are shown in each plot. FIG. 3F shows CD19 and Myc protein expression in the same cultures. FIG. 3G shows Myc levels in Pax5- and CD19-reconstituted cell lines following treatment with cycloheximide (CHX). CHX was added at the concentration of 1 μg/ml for 7.5-30 minutes. In the bottom panels Myc-specific bands were quantitated by densitometry, normalized to actin, and plotted against time after treatment. Note that different exposures are shown for parental and Pax5/CD19-transduced cells to allow accurate band quantitation. FIG. 3H shows steady-state Myc levels in the same cultures detected by radioimmunoprecipitation. Cells were pulse-labeled with $^{35}$S-methionine for 30 minutes followed by 0-30 minutes chase with "cold" amino acids.

FIG. 4 shows the analysis of short-term cultures of primary B-cells from wild-type and CD19-null mice. FIG. 4A shows flow cytometry of bone marrow cells that were cultured for 9 days and the percentages of B220- and CD19-positive cells. Numbers refer to relative abundances of predominant cell fractions. FIG. 4B shows flow cytometry of splenocytes from wild type mice were cultured for 3 days.

Figure 5:
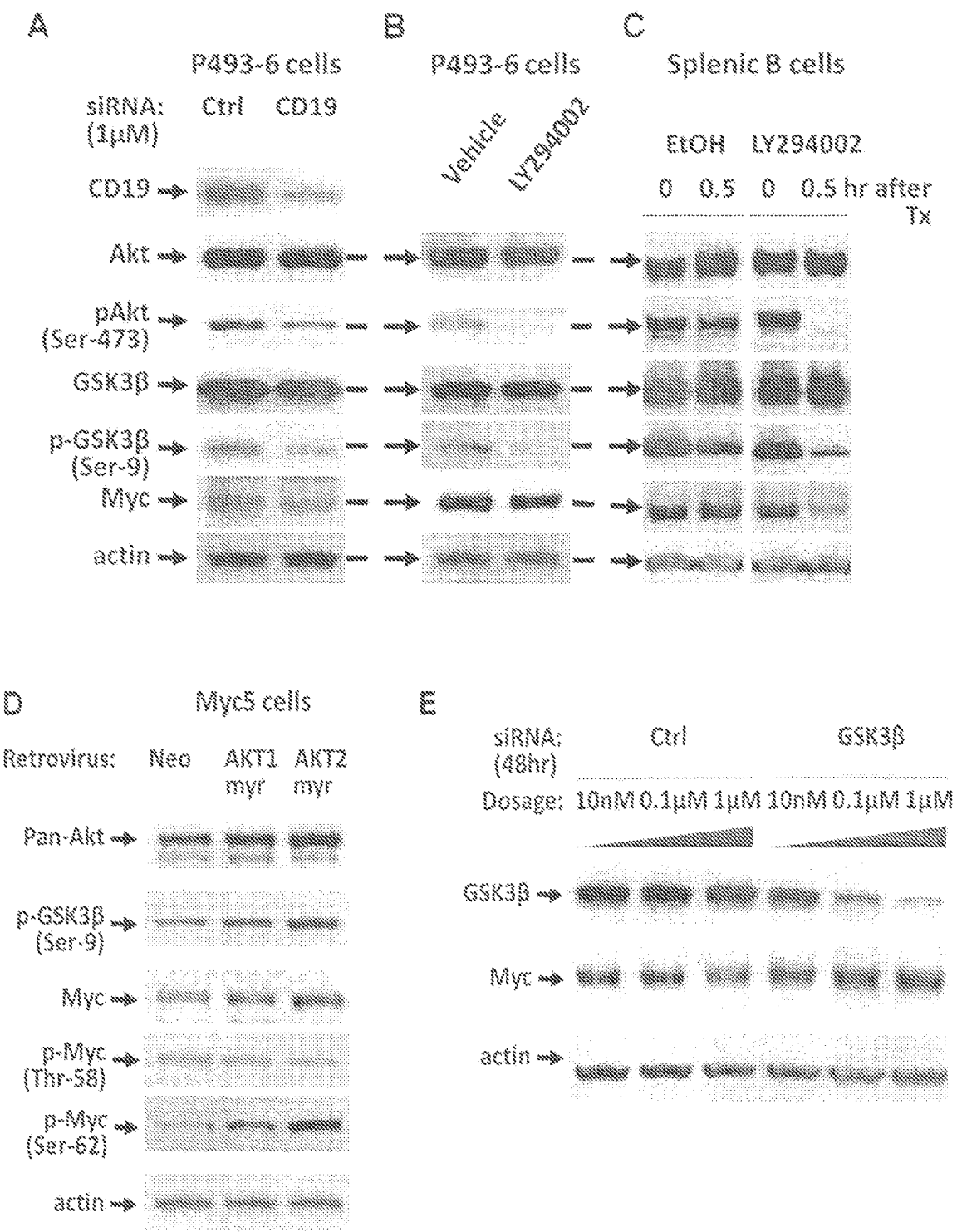
Figure 5:
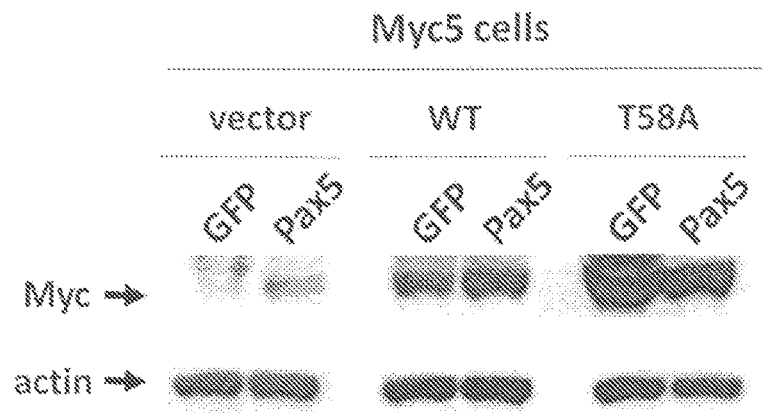
Figure 5:
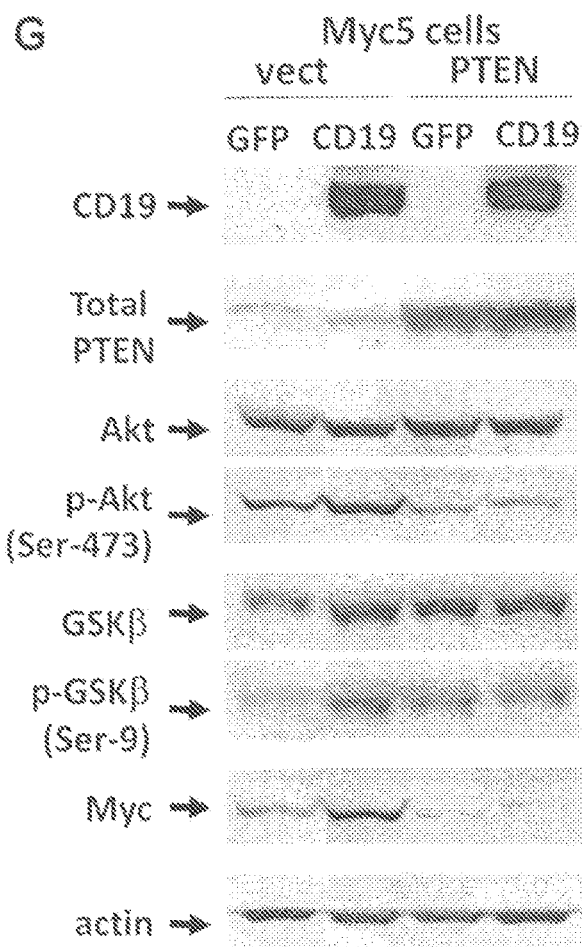

FIG. 5 shows that CD19 regulates Myc protein expression through the PI3K-AKT pathway. All panels represent immunoblotting analyses of proteins which belong to the CD19-PI3K pathway. Actin was used as a loading control. FIG. 5A shows P493-6 cells electroporated 24 hours prior to harvesting with 1 μM of control or anti-CD19 siRNA. FIG. 5B shows the same cells treated with 10 μM of PI3K inhibitor LY29004 or vehicle alone (ethanol) for 1 hour. FIG. 5C shows splenic B-cells pretreated with the same reagents for 0.5 hour. FIG. 5D shows Myc5 cells transduced with either empty retroviral vector (neo) or retroviruses expressing constitutively active forms of Akt1/2 (AKTmyr). Protein lysates were additionally probed with antibodies against Myc residues Thr-58 and Ser-62. FIG. 5E shows P493-6 cells electroporated 48 hours prior to harvesting with increasing concentrations of control or anti-GSK3β siRNA. FIG. 5F shows Myc5 cells expressing GFP or Pax5 that were additionally transduced with either empty vector, WT Myc or the T58A variant. Transduced cells were immunoblotted for Myc (top), and Myc protein levels in Pax5-transduced cells were compared to that in GFP-transduced cells. Note that the T58A variant has the Pyo-tag and thus migrates slower in SDS-PAGE gels. FIG. 5G shows Myc5 cells expressing GFP or CD19 from FIG. 3B that were additionally transduced with either empty vector or the PTEN-encoding retrovirus ("PTEN").

Figure 6:
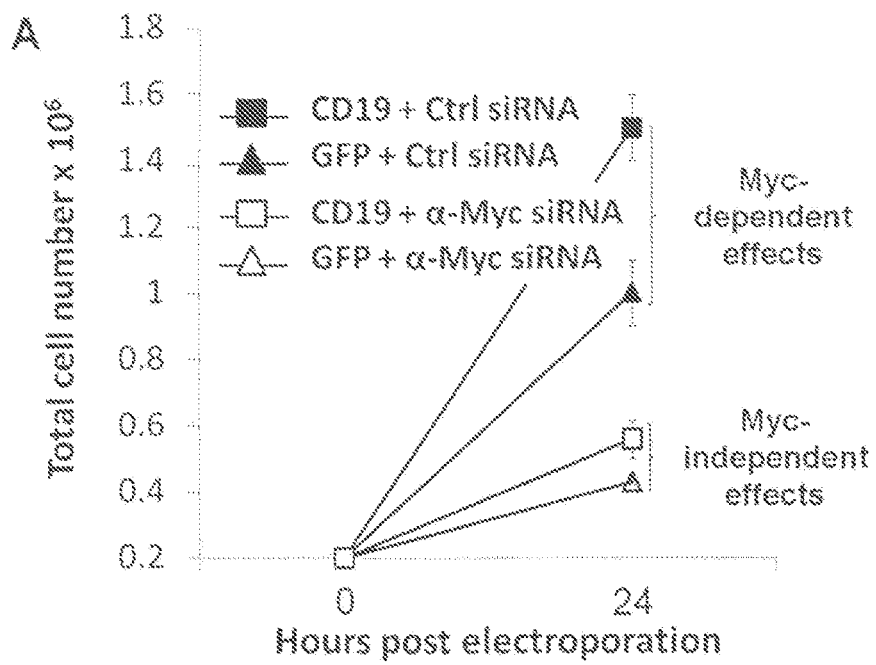
Figure 6:
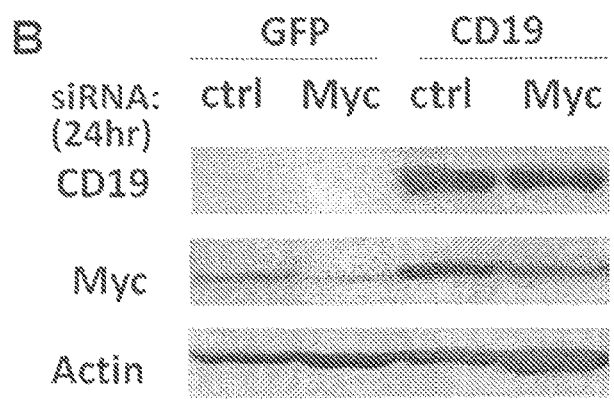
Figure 6:
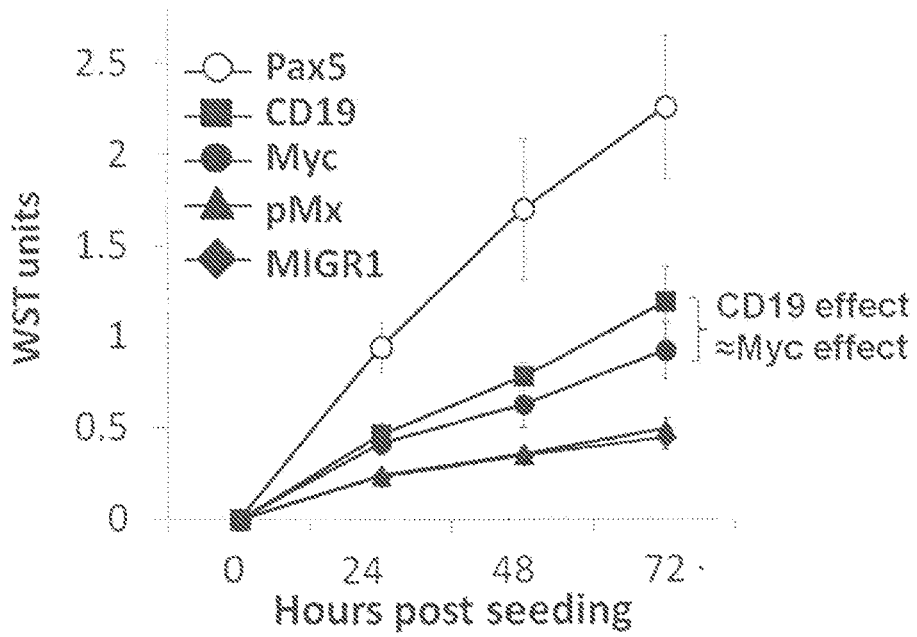
Figure 6:
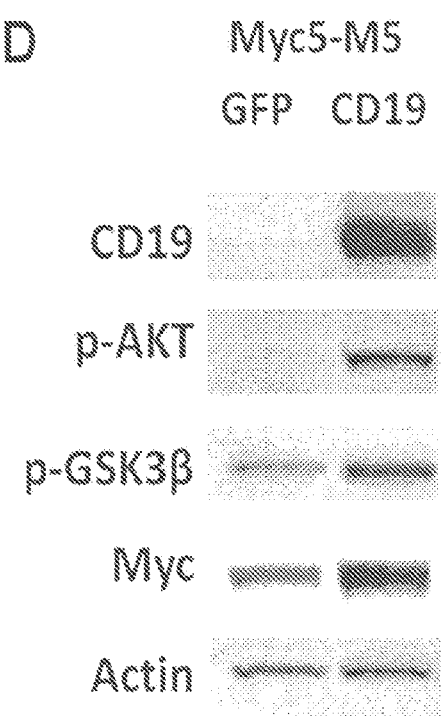
Figure 6:
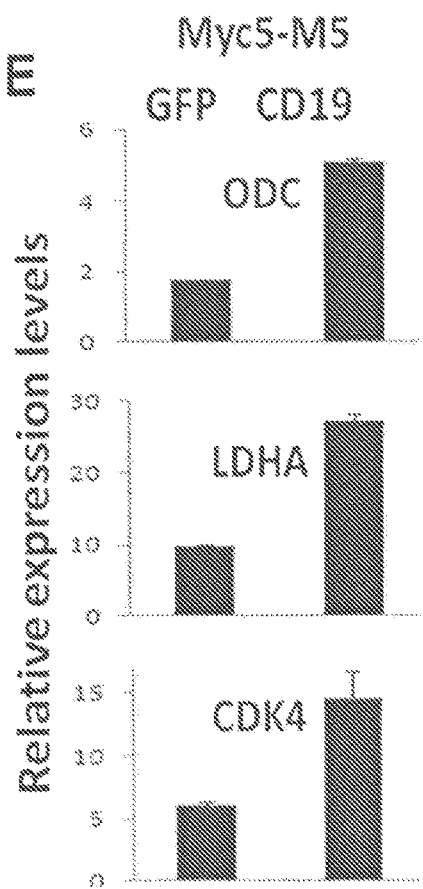
Figure 6:
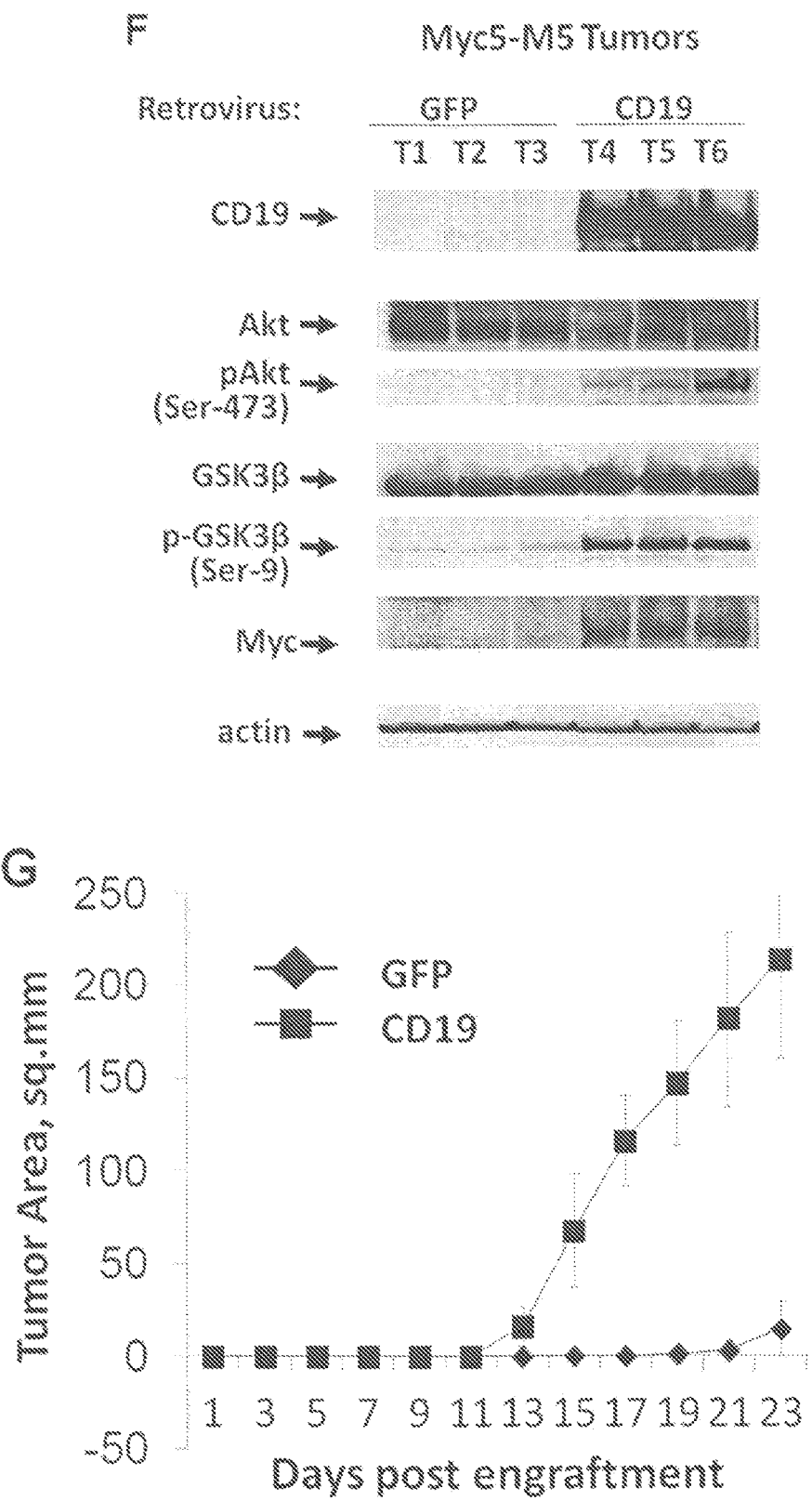

FIG. 6 shows that CD19 promotes cell expansion in vitro and tumor growth in vivo. Cell lines used in these experiments were either MYC5 (FIGS. 6A-6C) or its single-cell subclone Myc5-M5 (FIGS. 6D-6G). FIG. 6A shows comparative analysis of growth rates of control- and anti-Myc siRNA-treated GFP- and CD19-reconstituted MYC5 cultures. FIG. 6B shows Myc protein levels in the same cultures. FIG. 6C shows a comparative analysis of growth rates of Pax5-, CD19-, and Myc-reconstituted MYC5 cultures. FIG. 6D shows the expression levels of CD19-Myc axis component in CD19-reconstituted MYC5-M5 cells. FIG. 6E shows the levels of known Myc target genes in cultures from FIG. 6D. FIG. 6F shows the expression levels of CD19-Myc axis component in CD19-reconstituted MYC5-M5 tumors following subcutaneous engrafting in SCID mice. Three individual tumors from each cohort were randomly chosen for this analysis. FIG. 6G shows the growth rates of tumor xenografts from FIG. 6F. No less than 5 mice were analyzed in each group. Error bars denote standard deviations.

Figure 7A:
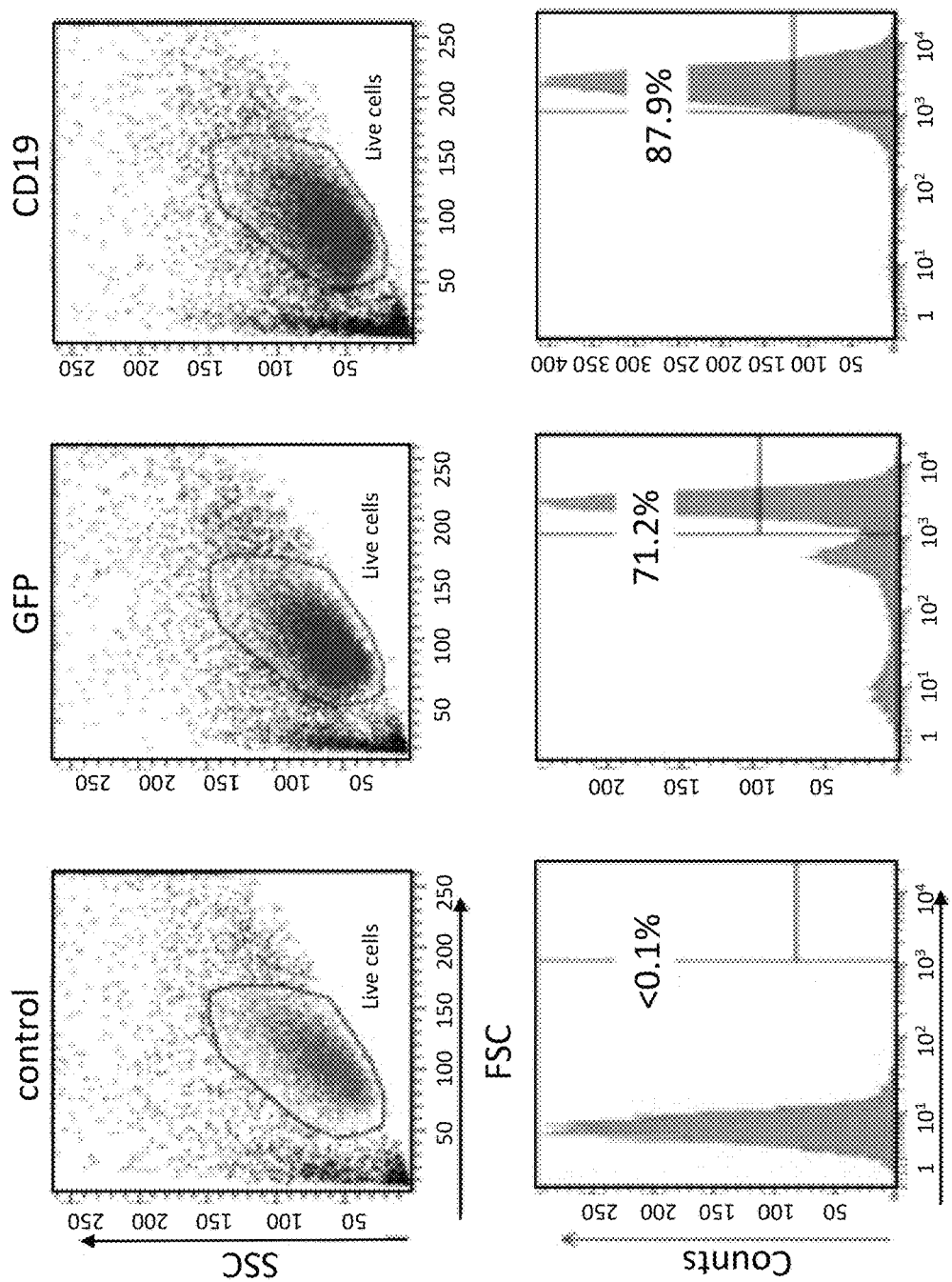
Figure 7B:
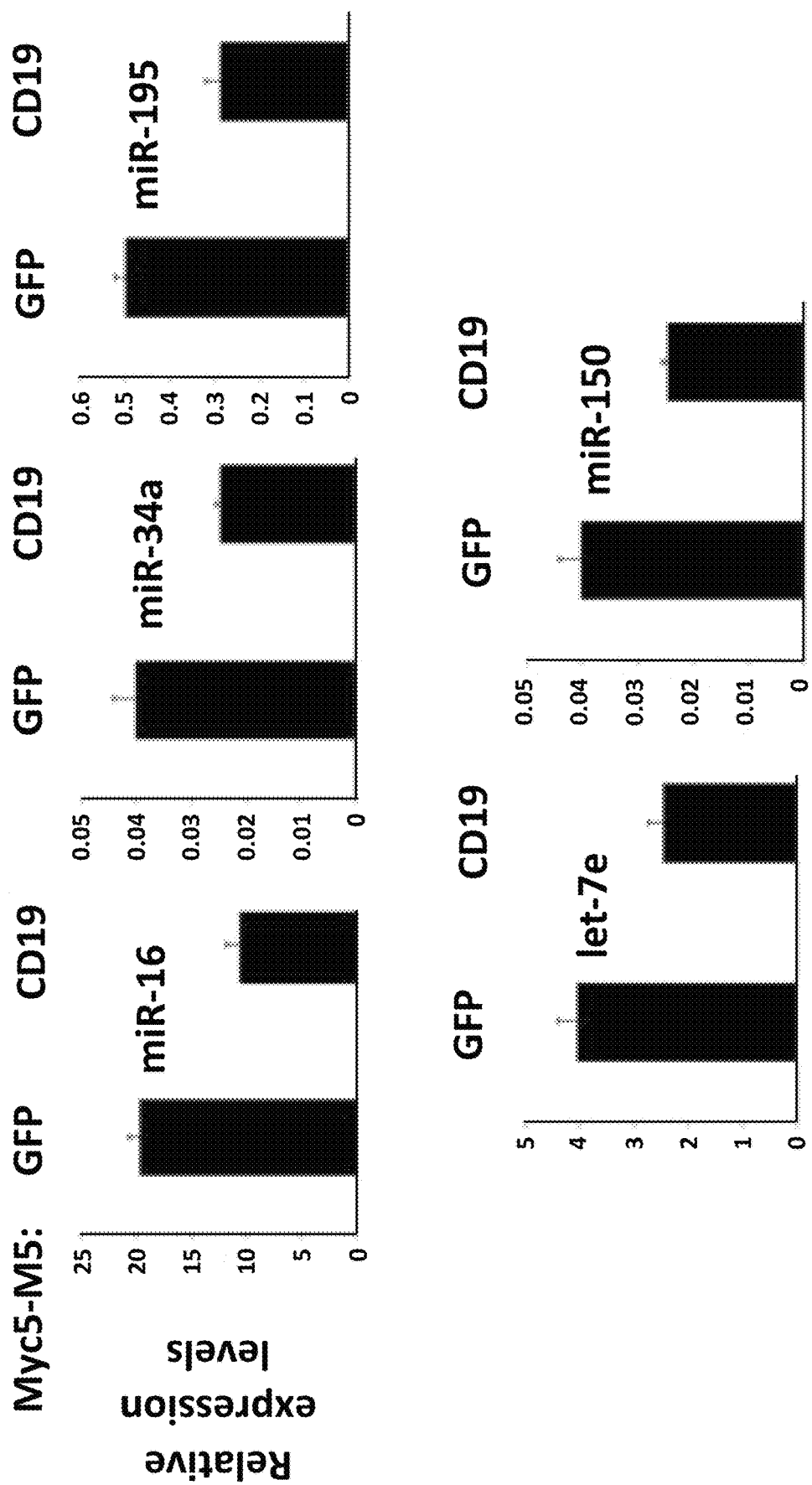

FIG. 7 shows the generation and analysis of CD19-expressing Myc5-M5 cells. Myc5-M5 cells were transduced with either empty vector (GFP) or the CD19-retrovirus. 24 hours post infection flow cytometry was performed determine the percentage of GFP-positive cells (FIG. 7A). These cells were subsequently sorted, expanded in vitro, and used for the experiments depicted in FIG. 6. Relative levels of key Myc-repressed microRNAs in control (GFP) and CD19-reconstituted Myc5-M5 cells are shown in FIG. 7B).

Figure 8A:
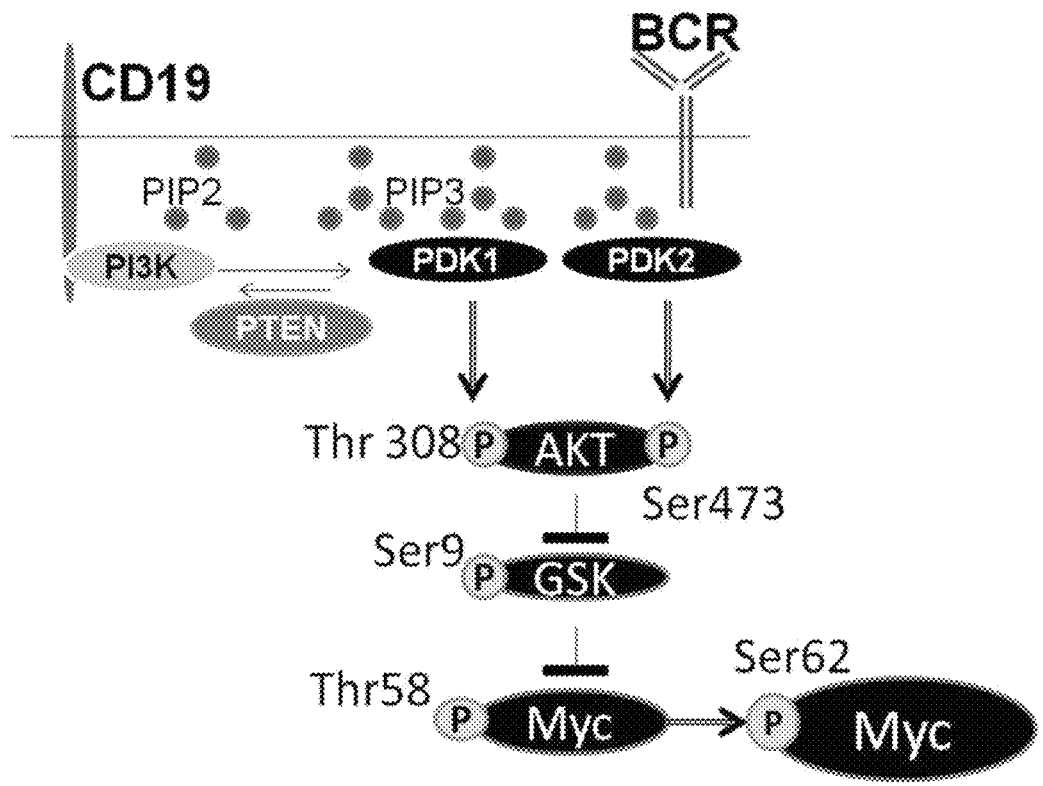
Figure 8B:
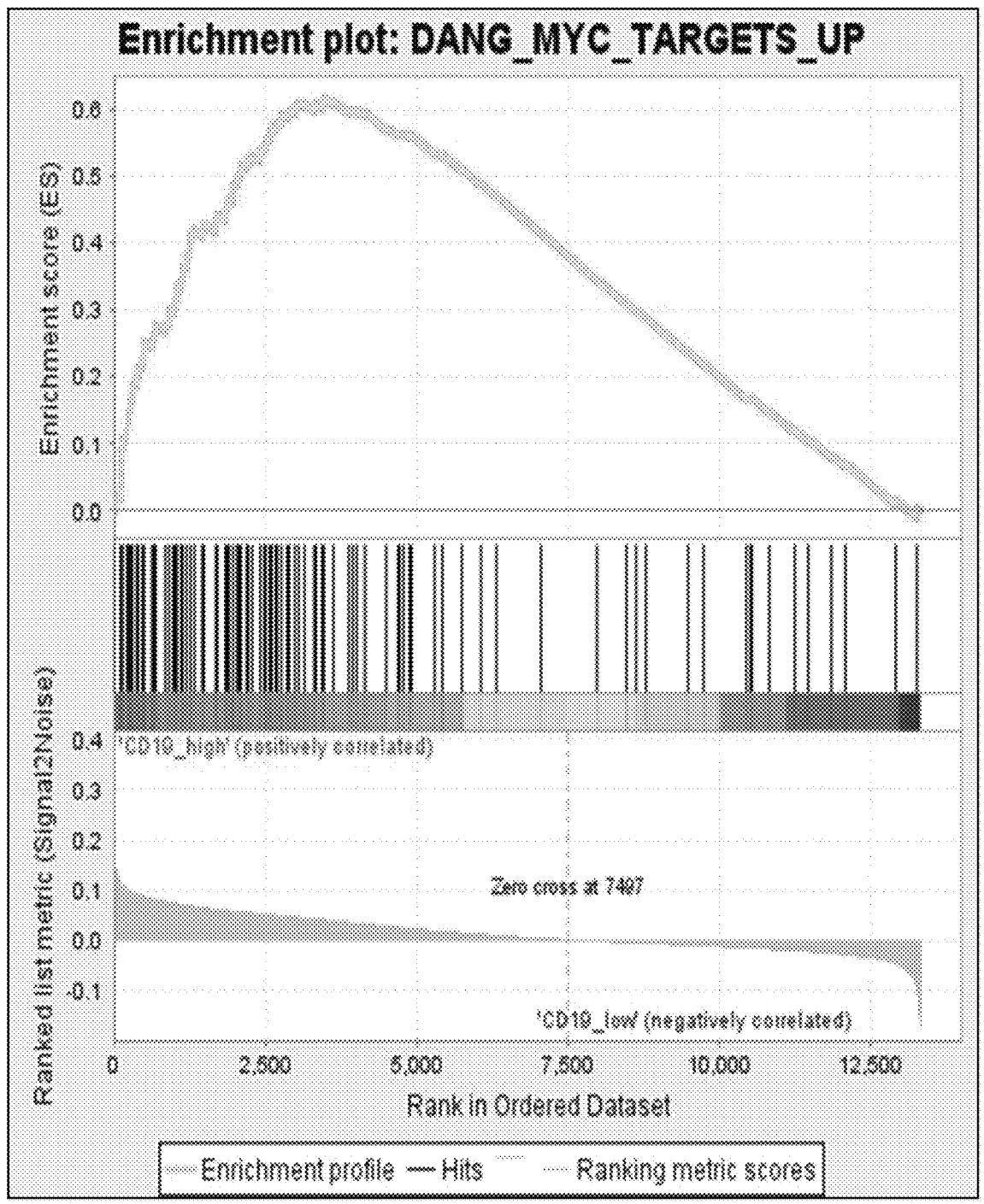
Figure 8:
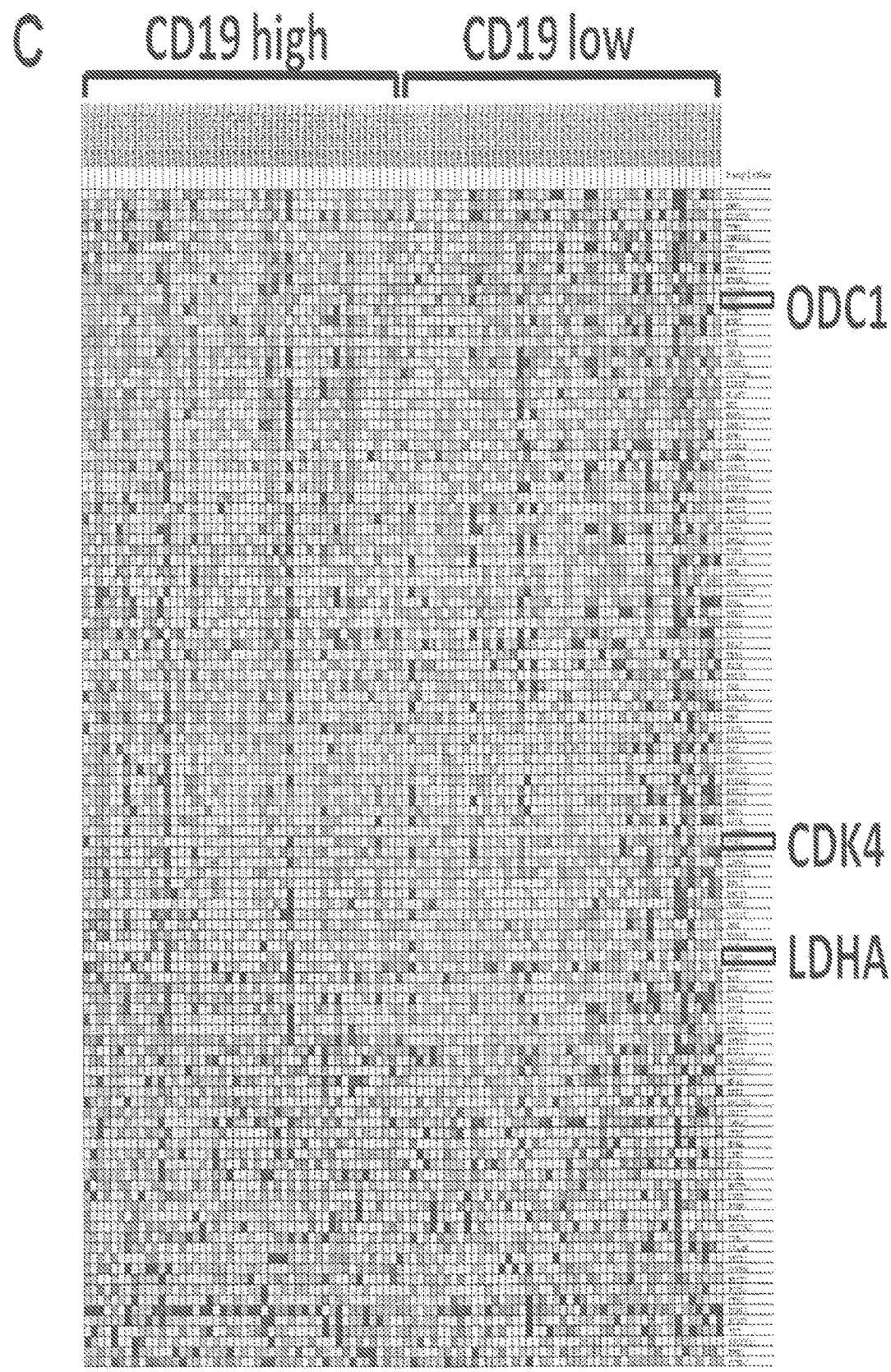
Figure 8:
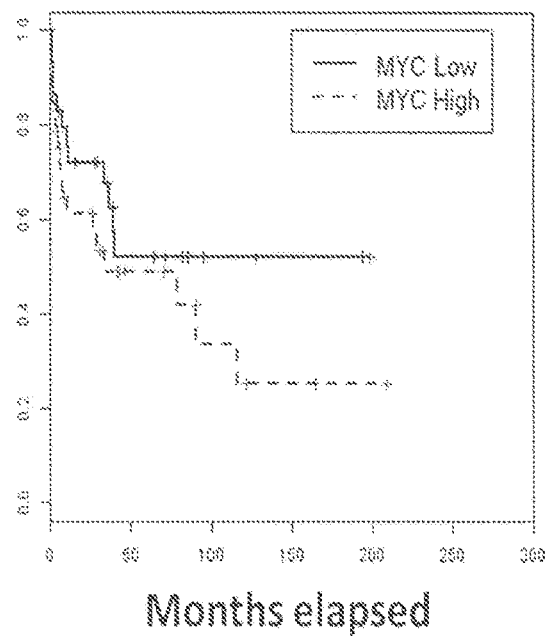
Figure 8:
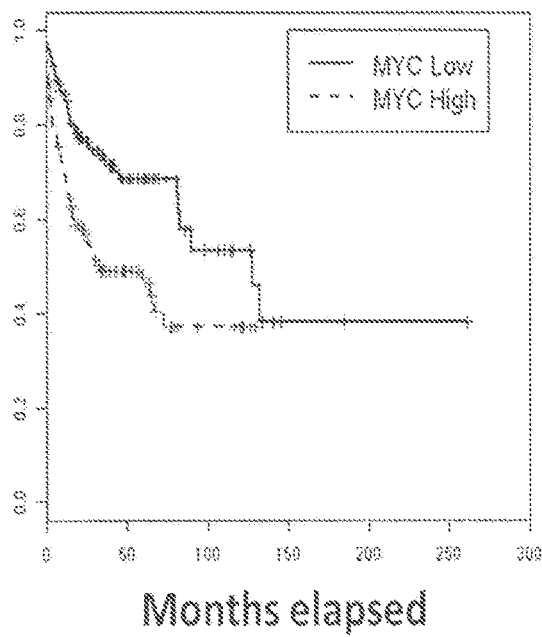
Figure 8:
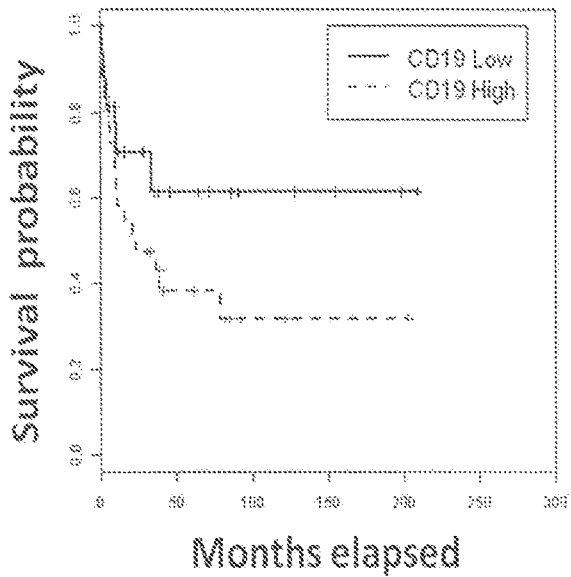
Figure 8:
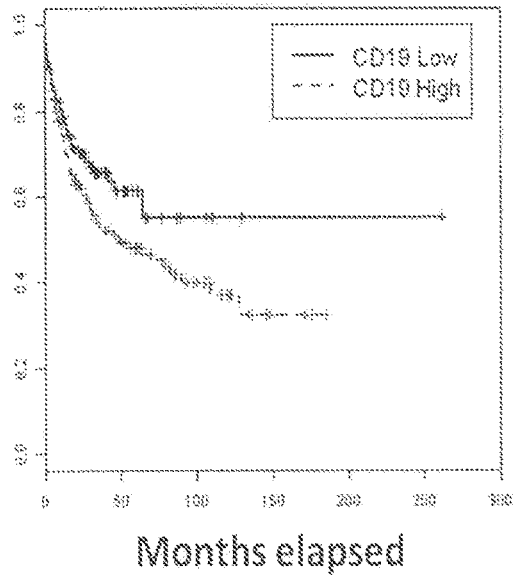

FIG. 8 shows that CD19 contributes to Myc function in human B-lymphomas. FIG. 8A provides the overall model whereby CD19 promotes Myc stabilization in a BCR-independent manner. FIG. 8B shows a GSEA enrichment plot for the DANG_MYC_TARGETS_UP set comparing $CD19^{HIGH}$ tumors to $CD19^{LOW}$ tumors. The Normalized Enrichment Score, p-value, and FDR q-value are indicated below the plot. FIG. 8C provides a heatmap generated during GSEA depicting the Myc target genes and comparing $CD19^{HIGH}$ tumors to $CD19^{LOW}$ tumors. FIG. 8D provides Kaplan-Meier curves comparing survival of $MYC^{HIGH}$ patients to $MYC^{LOW}$ patients in the Hummel (left panel) and Lenz (right panel) studies. FIG. 8E provides Kaplan-Meier curves comparing survival of $CD19^{HIGH}$ patients to $CD19^{LOW}$ patients in the Hummel (left panel) and Lenz (right panel) studies.

Figure 9:
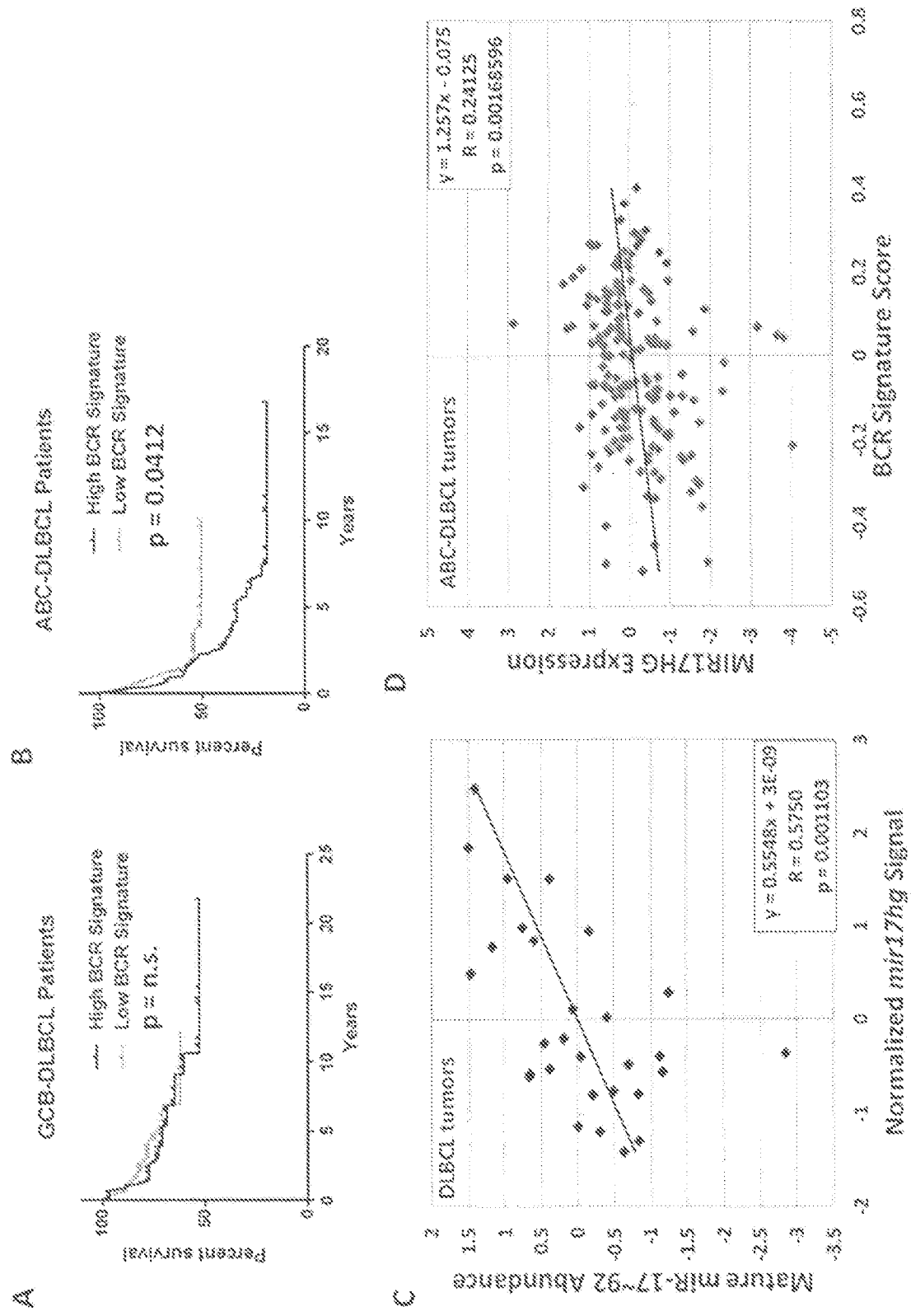
Figure 9:
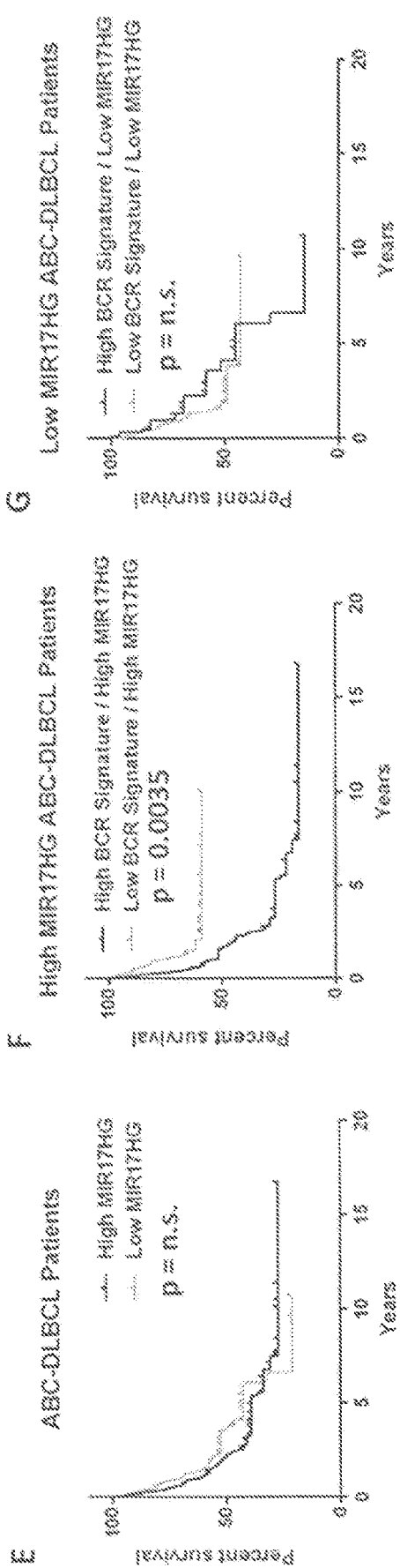

FIGS. 9A and 9B show percent survival over time of the indicated patients. FIG. 9C provides a graph showing the correlation between miR-17~92 abundance and mir17hg signal. FIG. 9D shows the correlation between the BCR signature and mir17hg expression. FIGS. 9E, 9F, and 9G provide graphs showing the percent survival over time of the indicated subjects.

Figure 10:
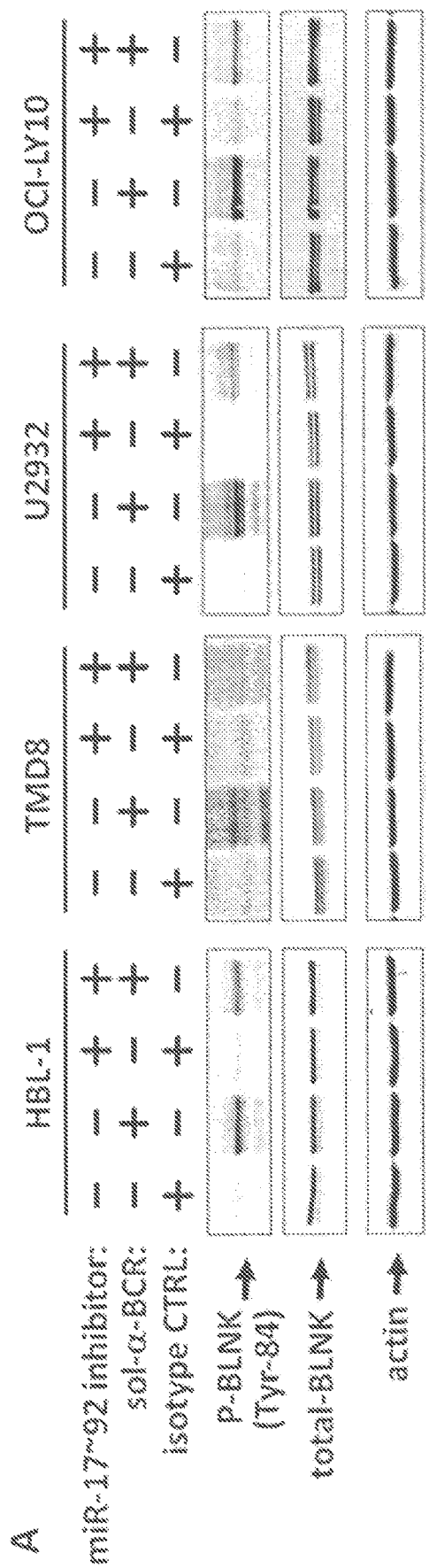
Figure 10:
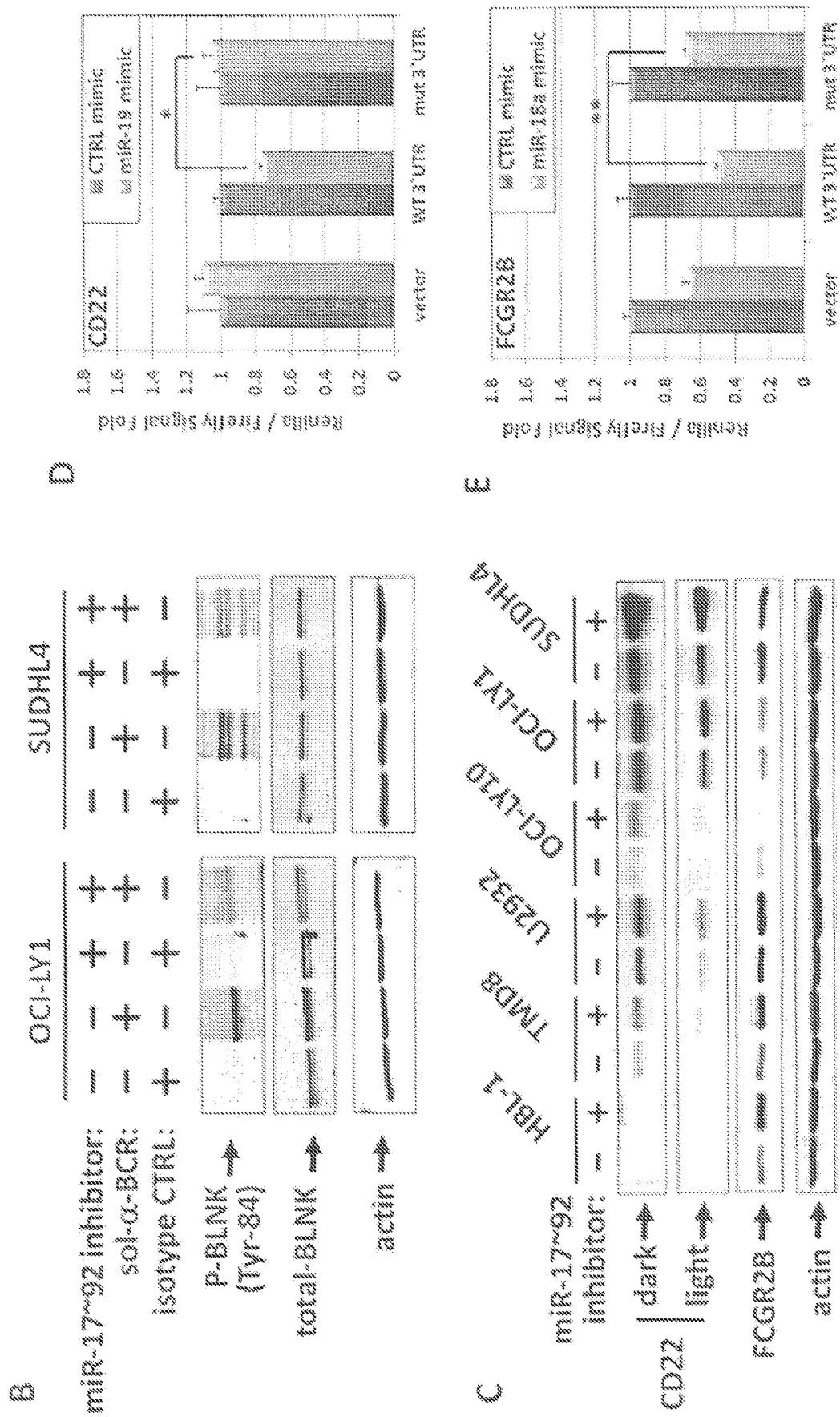
Figure 10:
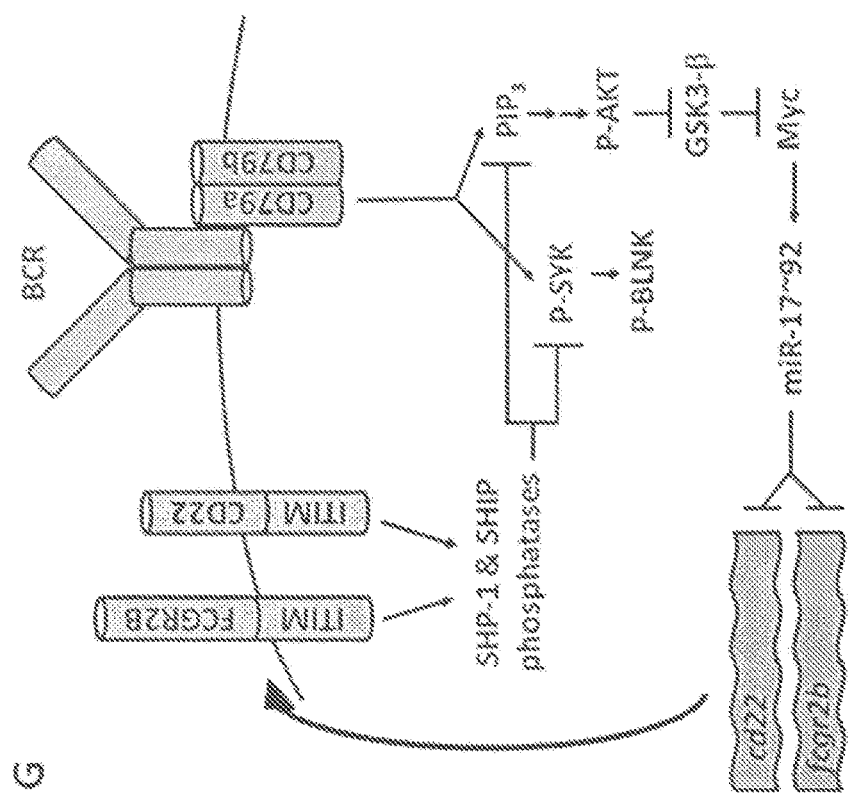
Figure 10:
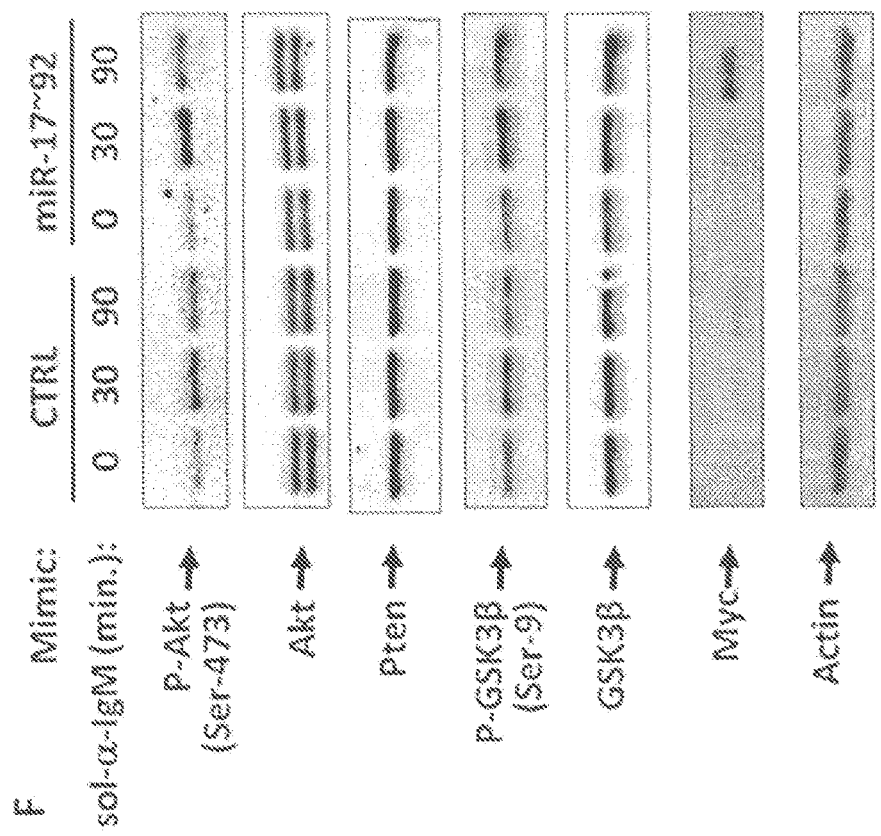

FIGS. 10A and 10B show the phosphorylation of BLNK in various cell types in the presence or absence of miR-17~92 inhibitor. FIG. 10C shows the expression of CD22 in various cells. FIGS. 10D and 10E provide graphs of the expression of luciferase in the presence or absence of the indicated miRNA. FIG. 10F shows the phosphorylation of Akt and GSK3β with or without miR17-92 mimic. FIG. 10G provides a schematic of the BCR response.

Figure 11:
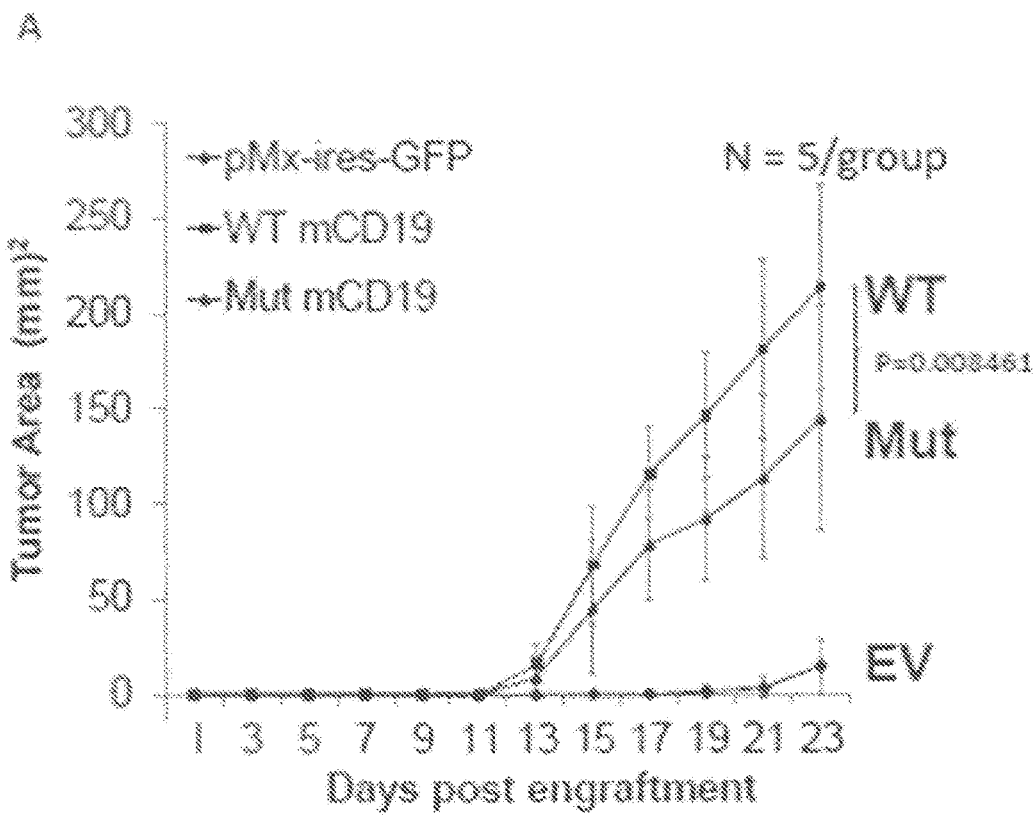
Figure 11:
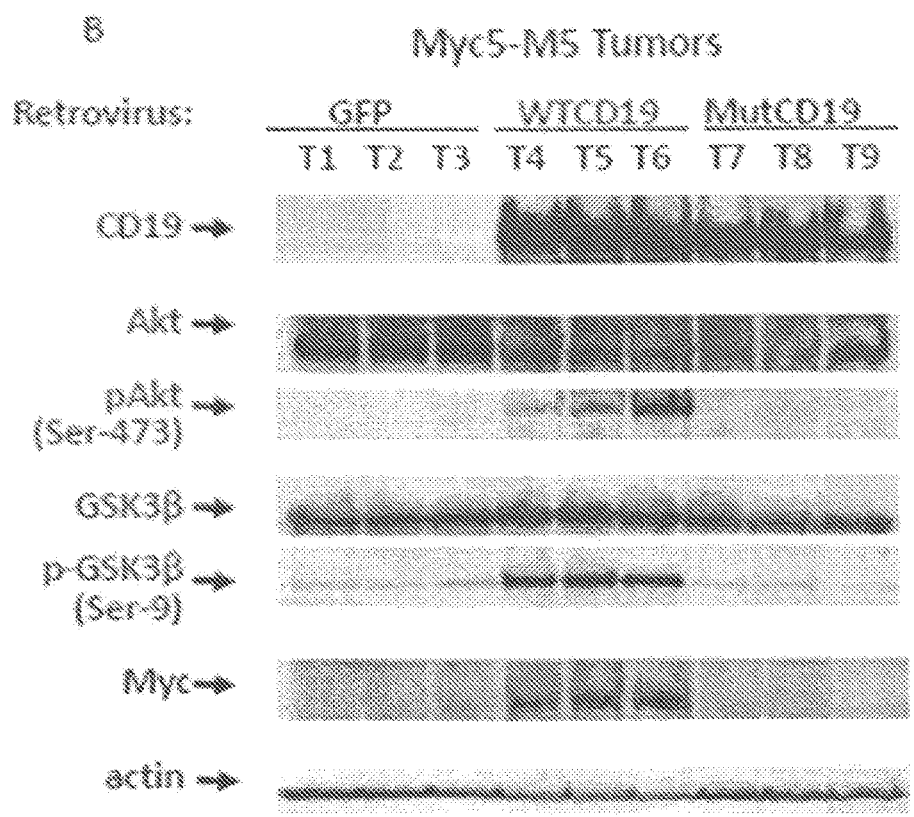

FIG. 11 shows that PI3K-disabled CD19 activates JNK and promotes tumor growth in vitro and in vivo. FIG. 11A provides growth rates of MYC5 tumors expressing either wild type or mutant CD19. FIG. 11B provides immunoblotts of protein lysates obtained from individual tumors in FIG.

Figure 11C:
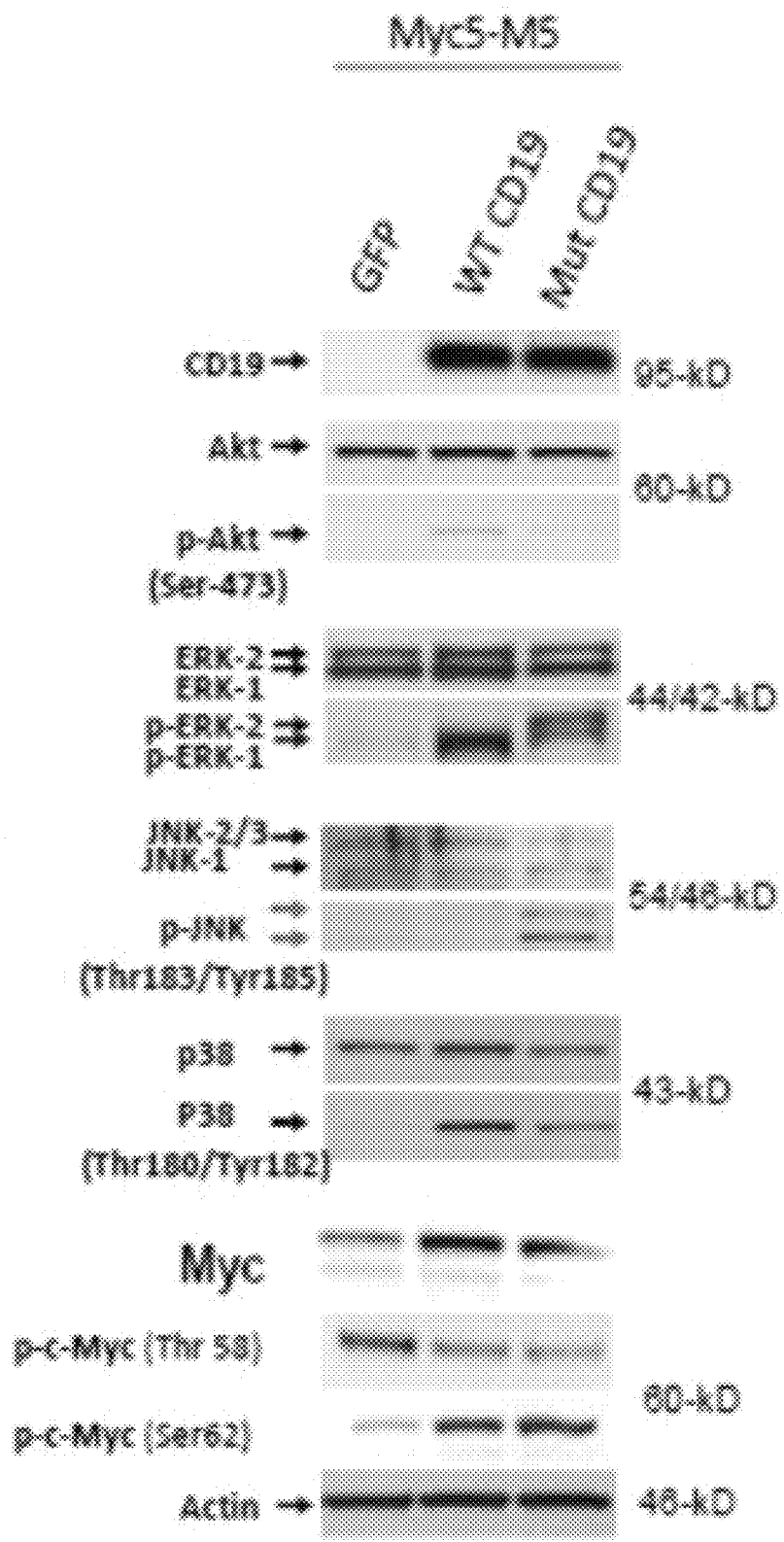
Figure 11E:
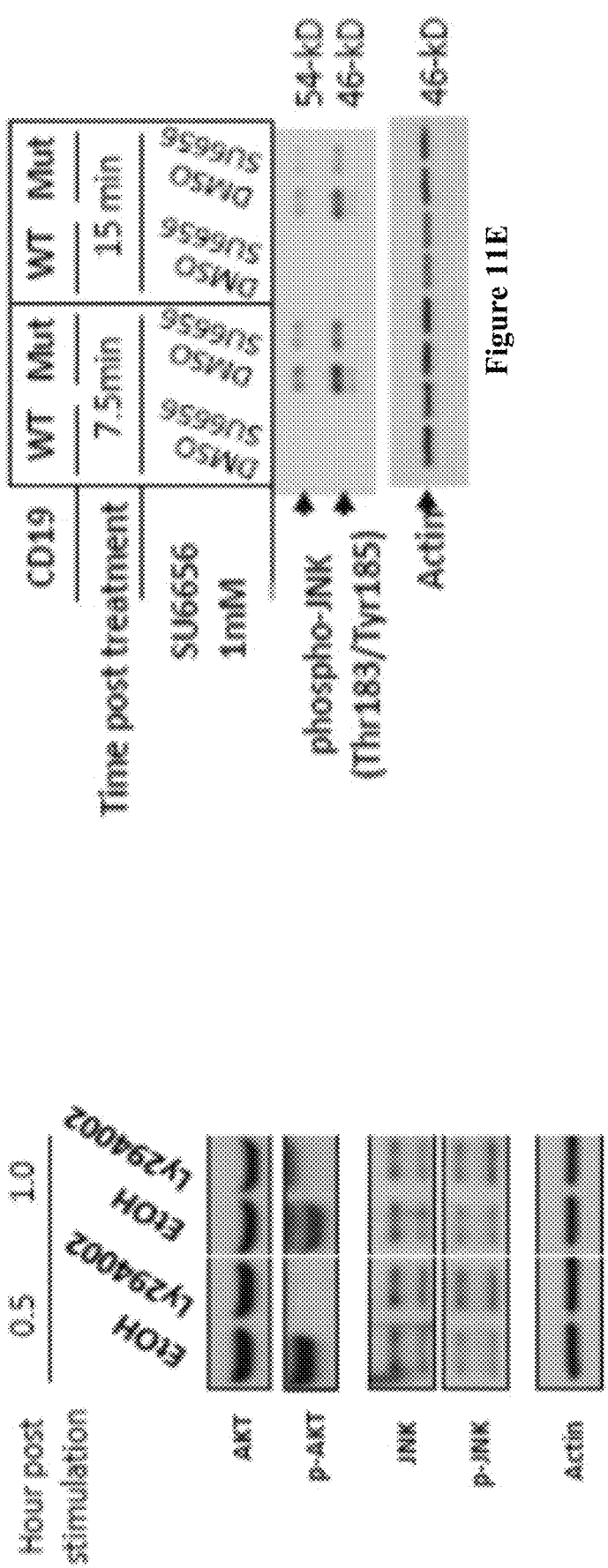
Figure 11F:
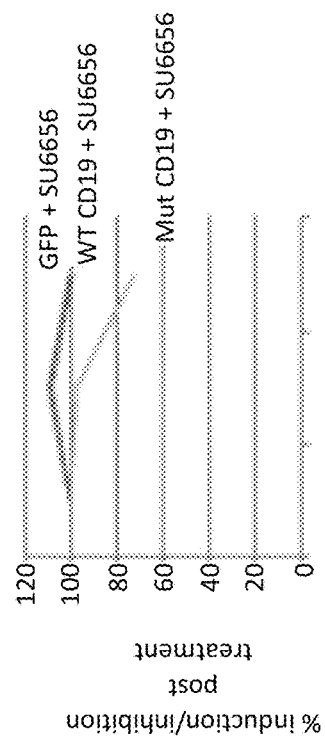
Figure 11D:
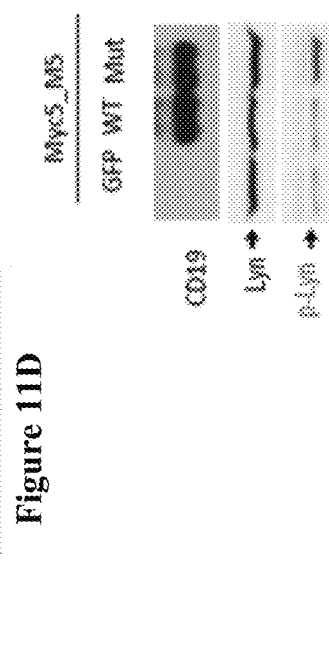

11A on day 23. FIG. 11C shows the phosphorylation of MAPK signaling molecules and their targets in response to wt or mutant CD19 reexpression in MYC5-M5 cells. FIG. 11D shows primary murine B cells treated with the PI3K inhibitor LY294002 or vehicle (EtOH). FIG. 11E shows MYC5 cells expressing either WT or MUTCD19 treated with SU6656 or vehicle only (DMSO) for the indicated time periods. Phosphorylation was assessed using Western blotting with phospho-specific antibodies. FIG. 11F shows the inhibition of MYC5/CD19 cell growth by SU6656. GFP-only-expressing MYC5 cells were used as a control. Cell proliferation was measured using the WST assay at indicated time points. FIG. 11F shows protein lysates from Myc_M5 (CD19-/BCR-) cells restored with either WT or MutCD19 immunoblotted with the antibodies listed.

FIG. 12 shows that B-ALL cells (BCR-CD19+) recruit the Src family tyrosine (SFTK) kinase Lyn and are sensitive to LYN inhibition. Lysates from B-ALL cells 697 and Burkitt's lymphoma cells P-4936 were subjected to immunoprecipitation with an anti-CD19 antibody or rabbit IgG (negative control). Immuno-precipitated proteins were then immunoblotted for PI3K or Lyn (FIG. 12A, top). Lysates from B-ALL cells 697 were immunoprecipitated with an anti-CD19 or Lyn antibody followed by immunoblotting for CD19 (FIG. 12A, bottom). CD19 shRNA treatment impairs Lyn phosphorylation and Myc expression and Lyn shRNA treatment reduces total and p-Lyn levels. Inhibition of Myc is also observed (FIG. 12B, top). FIG. 12B, bottom provides graphs of WST assays monitoring growth in CD19 (left) or Lyn (right) shRNA-treated cells. FIG. 12C shows annexin V/propidium iodide (PI) staining of cells treated with CD19 or Lyn shRNA and either Dasatinib at 100 nM concentration or vehicle (DMSO). FIG. 12D shows the efficacy of Dasatinib against Lyn. Protein lysates were harvested 0.5, 1.0, 2.0 and 4.0 hour post treatment for Western blot analysis (FIG. 12D, top). FIG. 12D also provides a graph of a WST assay monitoring cell growth following treatment with the drug. Cells were also harvested 48 hours post treatment for cell cycle analysis. Dasatinib arrests the cell cycle at the G1 phase, with the commensurate depletion of S and G2/M phases (FIG. 12D).

DETAILED DESCRIPTION OF THE INVENTION

One possible way to reconcile the oncogenic and tumor suppressor activities of Pax5 is that Pax5 affects neoplastic growth in a manner depending on stage differentiation and in particular—on BCR expression. As most NHLs are derived from mature and pre- and post-germinal center B-cells, they express this growth-promoting complex (Shaffer et al. (2002) Nat. Rev. Immunol., 2:920-932; Gururajan et al. (2006) J. Immunol., 176:5715-5719). In contrast, the vast majority of B-ALL (A1 and A2 types) are derived from immature pro- or pre-B-cells lacking BCR (Staudt, L. M. (2002) Cancer Cell 1:109-110). If transforming activity of Pax5 was dependent on BCR signaling, it would only manifest itself in NHL but not B-ALL, where intrinsic growth suppressive effects of Pax5 might be unmasked (Thomas-Tikhonenko et al. (2008) Future Oncol 4:5-9).

Indeed, the induction of BCR signaling is important for Myc-induced Pax5-mediated lymphomagenesis (Cozma et al. (2007) J. Clin. Inv., 117:2602-2610). Specifically, Pax5-dependent neoplastic growth could be reduced by overexpression of ITAM-specific CD22 phosphatase or treatment with Syk inhibitors, or mimicked by forced expression of the constitutively active ITAM construct (Grande et al. (2006) Oncogene 25:2748-2757). Subsequent data using transgenic mouse models validated the idea that Myc and BCR signaling pathways cooperate during B-lymphomagenesis (Refaeli et al. (2008) PLoS Biol 6:e152). Yet it remained unclear whether there is a direct functional interaction between the two key transcription factors, Myc itself and Pax5. This question was addressed using two cell models. One is the Myc5 cell line, derived from p53-null/Myc-induced murine lymphoma cells, which undergo spontaneous silencing of Pax5 when cultured in vitro (Cozma et al. (2007) J. Clin. Inv., 117:2602-2610; Yu et al. (2003) Blood 101:1950-1955; Johnson et al. (2004) Nat. Immunol., 5:853-861; Hodawadekar et al. (2006) J. Immunol., 177:6165-6171; Hodawadekar et al. (2007) Exp. Cell Res., 313:331-340). The other is P493-6 human B-lymphoblastoid cells immortalized by Epstein-Barr virus and expressing the Myc transgene from a tet-regulated promoter (Pajic et al. (2000) Int. J. Cancer 87:787-793; Clark et al. (1992) Science 258:123-126). In vivo and in vitro data obtained using these cell lines as well as primary murine B-cells and human non-Hodgkin lymphomas yielded the surprising conclusion that in B-cells Pax5 and its downstream effector CD19 are important post-transcriptional regulators of Myc protein levels. This finding has important implications for B-lymphomagenesis.

More specifically, using a MYC-induced murine lymphoma model as well as MYC-transformed human B cell lines, it is shown herein that PAX5 controls c-MYC protein stability and steady-state levels. This promoter-independent, posttranslational mechanism of c-MYC regulation was independent of ITAM/BCR activity. Instead it was controlled by another PAX5 target, CD19, through the PI3K-Akt-GSK3β axis. Consequently, MYC levels in B cells from CD19-deficient mice were sharply reduced. Conversely, reexpression of CD19 in murine lymphomas with spontaneous silencing of PAX5 boosted MYC levels, expression of its key target genes, cell proliferation in vitro, and overall tumor growth in vivo. In human B-lymphomas, CD19 mRNA levels were found to correlate with those of MYC-activated genes. They also negatively correlated with the overall survival of patients with lymphoma in the same way that MYC levels do. Thus, CD19 is a major BCR-independent regulator of MYC-driven neoplastic growth in B cell neoplasms.

Pax5 promotes B-lymphomagenesis (Thomas-Tikhonenko et al. (2008) Future Oncol., 4:5-9). Indeed, evidence includes the relatively rare but persistent t(9; 14) (p13; q32) translocation juxtaposing PAX5 and the IgH locus; somatic hypermutations of PAX5 in DLBCLs presumed to enhance Pax5 expression; and gene knock-down/overexpression studies (Cozma et al. (2007) J. Clin. Inv., 117:2602-2610; Cook et al. (2004) Hum. Pathol., 35:447-454; Busslinger et al. (1996) Proc. Natl. Acad. Sci., 93:6129-6134; Iida et al. (1996) Blood 88:4110-4117; Morrison et al. (1998) Blood 92:3865-3878; Poppe et al. (2005) Genes Chromosomes Cancer 44:218-223; Pasqualucci et al. (2001) Nature 412:341-346). Negative effects on B-cell expansion were also observed following knock-down of the Pax5 effector CD79a (Ig-α) in DLBCL cells lines (Gururajan et al. (2006) J. Immunol., 176:5715-5719). Since CD79a is the central structural component of the B-cell receptor (Monroe, J. G. (2006) Nat. Rev. Immunol., 6:283-294), these results suggested that stimulation of Ig-α/BCR signaling by Pax5 underlies its transforming activity. Indeed, constitutively active CD79a/b heterodimer (ITAM) also promotes B-lymphomagenesis (Cozma et al. (2007) J. Clin. Inv., 117:2602-2610; Refaeli et al. (2008) PLoS Biol 6:e152). The cooperation between BCR and Myc has also been observed, suggesting that they might be acting in parallel, not collinear pathways. Herein, it is shown that while restoration of Pax5 expression strongly augments Myc levels, ITAM has no appreciable effect on Myc levels. Instead this role could be ascribed to CD19-mediated signaling.

CD19 is a well-known B cell surface molecule, which upon BCR activation enhances B-cell antigen receptor-induced signaling crucial of the expansion of B-cell population (Tedder, T. F. (2009) Nat. Rev. Rheumatol., 5:572-577). One known mechanism of its action is the recruitment and activation of PI3 and subsequently Akt kinases (Tuveson et al. (1993) Science 260:986-989; Buhl et al. (1999) J. Immunol., 162:4438-4446; Otero et al. (2001) J. Biol. Chem., 276:1474-1478; Fujimoto et al. (2002) J. Immunol., 168:5465-5476; Aiba et al. (2008) Blood 111:1497-1503). This is accomplished through the docking function of two tyrosine residues, Y482 and Y513, in the cytoplamic region of CD19 (Wang et al. (2002) Immunity 17:501-514). Furthermore, inhibitory phosphorylation by Akt of GSK3β on Ser-9 is one of the key functions of this pathway (Cross et al. (1995) Nature 378:785-789). In turn, phosphorylation of Myc on Thr-58 by GSK3l3 leads to enhanced recognition by the Fbw7 E3 ubiquitin ligase and accelerated protein degradation (Hann, S. R. (2006) Semin. Cancer Biol., 16:288-302; Welcker et al. (2004) Proc. Natl. Acad. Sci., 101:9085-9090; Pulverer et al. (1994) Oncogene 9:59-70). However, Myc protein stability is controlled extensively by other phosphorylation sites and other ubiquitin ligases (Hann, S. R. (2006) Semin. Cancer Biol., 16:288-302; Sears, R. C. (2004) Cell Cycle 3:1133-1137). Hence it was surprising to find herein that in B-cells inactivation of GSK3β has such profound effects on Myc protein levels (see FIG. 5E). The other surprising result was that stimulation of Akt signaling by CD19 (see FIG. 5G) was observed in cells lacking the core BCR component CD79a (Ig-α) and thus was completely independent of B-cell receptor signaling which is known to control survival of mature B-lymphocytes (Srinivasan et al. (2009) Cell 139:573-586; Patterson et al. (2006) Immunity 25:55-65; Kraus et al. (2004) Cell 117: 787-800).

CD19 not only augments Myc levels, it clearly has a positive effect on Myc function. For example, Myc5-M5 cells reconstituted with CD19 exhibit elevated levels of Myc targets ODC1, CDK4, and LDHA (see FIG. 6E). Moreover, in human DLBCLs there is a highly statistically significant correlation between CD19 mRNA levels and that of Myc-activated genes (see FIG. 8B, 8C) including ODC1, CDK4, and LDHA. Thus, CD19 levels in DLBCL negatively correlate with patients' survival, just like MYC levels do (see FIG. 8D, 8E).

CD19 (Cluster of Differentiation 19; Gene ID: 930; UniProtKB/Swiss-Prot: P15391.6; GenBank Accession No. P15391) is broadly expressed in both normal and neoplastic B-cells. Because B-cell neoplasms frequently maintain Pax5 and CD19 expression, it (along with CD20) is regarded as the target of choice for a variety of immunotherapeutic agents, including immunotoxins (Scheuermann et al. (1995) Leuk. Lymphoma 18:385-397; Tedder, T. F. (2009) Nat. Rev. Rheumatol., 5:572-577). In particular, humanized anti-CD19 mAbs and allogeneic T-cells expressing chimeric antibody receptor for CD19 have entered clinical trials. They are presumed to work by recognizing and depleting CD19-expressing neoplastic B-cells (Davies et al. (2010) Cancer Res., 70:3915-3924; Awan et al. (2010) Blood 115:1204-1213). Notably, treatment with anti-CD19 antibodies typically results in internalization of CD19 and by inference—loss of its function (Sapra et al. (2004) Clin. Cancer Res., 10:2530-2537). Thus, in addition to delivering the anti-cancer drug or T-cells, conjugated anti-CD19 antibodies are likely to reduce PI3K signaling and as a result compromise Myc expression.

Notably, what drives cell proliferation in CD19-negative B-cell neoplasms such as multiple myelomas (MM), which are derived from plasma cells, is unclear. Interestingly, Myc rearrangements are very common in this disease, and recently described inhibitors of Myc gene transcription (JQ1) were used to demonstrate the essential role of Myc in MM pathogenesis (Chng et al. (2011) Leukemia 25:1026-1035; Shou et al. (2000) Proc. Natl. Acad. Sci., 97:228-233; Delmore et al. (2011) Cell 146:904-917). Myc levels may be sustained in MM in the absence of CD19 through 1) a rearranged allele that drives such robust transcription that the Myc protein can accumulate to sufficient levels even in the absence of PI3K signaling or 2) surface receptors other than CD19 are responsible for PI3K activation in MM (and other CD19-negative neoplasms such as Hodgkin's lymphoma). The second option is supported by the observation that at least in vitro MM cells are highly sensitive to PI3K inhibitors (Khwaja, A. (2010) Curr. Top. Microbiol. Immunol., 347:169-188), which could be through destabilization of Myc, the key oncoprotein in neoplasms of B-cell origin.

In accordance with the instant invention, methods of identifying chemotherapeutic agents (e.g., inhibitors of the CD19-PI3K interaction) are provided. The CD19 cytoplasmic tail comprises multiple tyrosine residues available for phosphorylation (e.g., Brooks et al. (2000) J. Immunol., 164:3123-3131). The p85 subunit of PI3K has been shown to interact with tyrosines 482 and 513 of the CD19 cytoplasmic tail (Brooks et al. (2004) J. Immunol., 172:7556-7564; Chen et al. (2007) Mol. Cell Biol., 27:3109-3122; Fujimoto et al. (2000) Immunity 13:47-57; O'Rourke et al. (1998) Immunity 8:635-645; Tuveson et al. (1993) Science 260:986-989). In a particular embodiment, the screening methods of the instant invention comprise performing a binding assay in the presence of at least one test compound to identify inhibitors which disrupt and/or prevent the interaction between CD19, particularly the cytoplasmic tail, and PI3K. The binding assay may be cell-based (e.g., yeast two hybrid assay). The binding assay may also comprise suitable controls such as performing the assay in the absence of a test compound and/or in the presence of a known inhibitor. Binding assays include, without limitation, cell surface receptor binding assays, fluorescence energy transfer assays, liquid chromatography, membrane filtration assays, ligand binding assay, radiobinding assay, immunoprecipitations, radioimmunoassays, enzyme-linked immunosorbent assays (ELISA), immunohistochemical assays, Western blot, and surface plasmon resonance. In a particular embodiment, either CD19 or PI3K is immobilized (e.g., to a solid support) in the binding assay and the amount of the other protein bound to the immobilized protein is measured in the presence of the test compound, particularly after washing away any unbound protein. In a particular embodiment, the assay is a cell-based screening assay. For example, compounds may be screened on B-cells in the presence of a ligand of CD19 (e.g., CD19-L (Uckun et al. (2011) Br. J. Haematol., 153:15-23), antibody against IgM, which comprises BCR). The ability of the compounds to inhibit CD19 interacting with/activating PI3K or downstream proteins may be screened for (see, e.g., FIG. 8A; e.g., decrease in Myc protein levels; decrease in Akt phosphorylation, decrease in GSK3β phosphorylation, etc.).

In a particular embodiment, the test compound is an antibody, small molecule or a peptide, particularly a peptide that mimics the binding domain of either CD19 or PI3K. The peptide may be about 5 to about 50 amino acids in length, particularly about 5 to about 10, 15, or 20 amino acids in length, having sequence identity (e.g., at least 90%, 95%, or 100% identity) with one of the proteins. For example, the peptide may comprise a sequence encompassing tyrosines 482 and/or 513 of the CD19 cytoplasmic tail (e.g., wherein the tyrosine residue(s) is within about the middle third of the peptide).

In accordance with the instant invention, methods of inhibiting (e.g., reducing), preventing, and/or treating cancer are provided. In a particular embodiment, the cancer is CD19 positive. In a particular embodiment, the cancer is CD-19 positive multiple myeloma. In a particular embodiment, the cancer is a B-cell neoplasm. B-cell neoplasms include, without limitation, lymphoma, non-Hodgkin's lymphoma, B-cell acute lymphoblastic leukemia, and chronic lymphocytic leukemia. In a particular embodiment, the method comprises administering at least one inhibitor of the CD19-PI3K interaction to a subject in need thereof. In a particular embodiment, the method comprises the administration of at least one Src family tyrosine kinase inhibitor, particularly a Lyn inhibitor (e.g., dasatinib, PP2) to a subject in need thereof. The CD19-PI3K inhibitor may be identified by the methods described hereinabove. In a particular embodiment, the inhibitor of the CD19-PI3K interaction is a small molecule, peptide, or antibody. In a particular embodiment, the antibody causes CD19 internalization, particularly without the elimination of CD19-positive cells. In a particular embodiment, the antibody is an intracellular antibody (intrabody; Lo et al. (2008) Handb. Exp. Pharmacol., 181:343-73), particularly an antibody (e.g., scFv) immunologically specific for the binding domain on PI3K or CD19 (e.g., the cytoplasmic domain; e.g., an epitope encompassing tyrosines 482 and/or 513).

The methods may further comprise the administration of at least one other cancer therapy (simultaneously and/or sequentially (before and/or after)) such as radiation therapy and/or the administration of at least one other chemotherapeutic agent. In a particular embodiment, the method further comprises the further administration of an anti-CD20 antibody (e.g., rituximab). In a particular embodiment, the method further comprises the further administration of at least one PI3K inhibitor (e.g., wortmannin, PX-866, LY294002). In a particular embodiment, the method further comprises the further administration of an anti-CD19 antibody (e.g., MEDI-551 (MedImmune) or XmAb5574 (MorphoSys)) or chimeric antigen receptors and/or cells targeting CD19. Chimeric antigen receptors typically comprise at least the antigen recognition domain of an antibody and an intracellular domain (e.g., a T-cell activation domain). In a particular embodiment, the method further comprises enhancing the expression and/or function of at least one immunoreceptor tyrosine inhibitory motif (ITIM) protein (e.g., CD22 or FCGR2B) (e.g., by delivering a nucleic acid molecule encoding the ITIM protein (e.g., as a vector, particularly a viral vector (e.g., gene therapy)). In a particular embodiment, the method further comprises targeting or inhibiting miR-17~92 and/or its downstream effectors such as BLNK and SYK (e.g., via inhibitory nucleic acid molecules (e.g., antisense oligonucleotides, siRNA, shRNA, etc.). In a particular embodiment, the method further comprises the administration of at least one Src family tyrosine kinase inhibitor, particularly a Lyn inhibitor (e.g., dasatinib, PP2), particularly when co-administered with a PI3K inhibitor. In a particular embodiment, the method further comprises the administration of at least one Myc inhibitor (e.g., a bromodomain inhibitor (e.g., JQ1); 10058-F4), particularly when co-administered with a Lyn inhibitor and/or PI3K inhibitor.

The present invention encompasses compositions comprising 1) at least one CD19-PI3K inhibitor and 2) at least one pharmaceutically acceptable carrier. Such compositions may be administered, in a therapeutically effective amount, to a patient in need thereof for the treatment of cancer. The compositions may further comprise one other chemotherapeutic agent. Alternatively, the other chemotherapeutic agent may be contained within a separate composition with at least one pharmaceutically acceptable carrier for sequential and/or simultaneous administration. Composition(s) of the instant invention may be contained within a kit.

Chemotherapeutic agents are compounds that exhibit anticancer activity and/or are detrimental to a cell (e.g., a toxin). Suitable chemotherapeutic agents include, but are not limited to: toxins (e.g., saporin, ricin, abrin, ethidium bromide, diphtheria toxin, Pseudomonas exotoxin, and others listed above; thereby generating an immunotoxin when conjugated or fused to an antibody); monoclonal antibody drugs (e.g., rituximab, cetuximab); alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nitroso ureas such as carmustine, lomustine, and streptozocin; platinum complexes such as cisplatin and carboplatin; bioreductive alkylators such as mitomycin, procarbazine, dacarbazine and altretamine); DNA strand-breakage agents (e.g., bleomycin); topoisomerase II inhibitors (e.g., amsacrine, dactinomycin, daunorubicin, idarubicin, mitoxantrone, doxorubicin, etoposide, and teniposide); DNA minor groove binding agents (e.g., plicamydin); antimetabolites (e.g., folate antagonists such as methotrexate and trimetrexate; pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, vinblastine, and paclitaxel (Taxol)); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); and antihormonal antigens (e.g., tamoxifen, antiandrogen agents such as flutamide; and antiadrenal agents such as mitotane and aminoglutethimide).

The compositions of the present invention can be administered by any suitable route, for example, by injection (e.g., for local (direct, including to or within a tumor) or systemic administration), oral, pulmonary, topical, nasal or other modes of administration. The composition may be administered by any suitable means, including parenteral, intramuscular, intravenous, intraarterial, intraperitoneal, subcutaneous, topical, inhalatory, transdermal, intrapulmonary, intraareterial, intrarectal, intramuscular, and intranasal administration. In a particular embodiment, the composition is administered intravenously. In general, the pharmaceutically acceptable carrier of the composition is selected from the group of diluents, preservatives, solubilizers, emulsifiers, adjuvants and/or carriers. The compositions can include diluents of various buffer content (e.g., Tris HCl, acetate, phosphate), pH and ionic strength; and additives such as detergents and solubilizing agents (e.g., Tween® 80, Polysorbate 80), anti oxidants (e.g., ascorbic acid, sodium metabisulfite), preservatives (e.g., Thimersol, benzyl alcohol) and bulking substances (e.g., lactose, mannitol). The compositions can also be incorporated into particulate preparations of polymeric compounds such as polyesters, polyamino acids, hydrogels, polylactide/glycolide copolymers, ethylenevinylacetate copolymers, polylactic acid, polyglycolic acid, etc., or into liposomes. Such compositions may influence the physical state, stability, rate of in vivo release, and rate of in vivo clearance of components of a pharmaceutical composition of the present invention. See, e.g., Remington: The Science and Practice of Pharmacy, $21^{st}$ edition, Philadelphia, Pa. Lippincott Williams & Wilkins. 2005. The pharmaceutical composition of the present invention can be prepared, for example, in liquid form, or can be in dried powder form (e.g., lyophilized for later reconstitution).

As used herein, "pharmaceutically acceptable carrier" includes any and all solvents, dispersion media and the like which may be appropriate for the desired route of administration of the pharmaceutical preparation, as exemplified in the preceding paragraph. The use of such media for pharmaceutically active substances is known in the art. Except insofar as any conventional media or agent is incompatible with the molecules to be administered, its use in the pharmaceutical preparation is contemplated.

The dose and dosage regimen of the molecule of the invention that is suitable for administration to a particular patient may be determined by a physician considering the patient's age, sex, weight, general medical condition, and the specific condition and severity thereof for which the inhibitor is being administered. The physician may also consider the route of administration, the pharmaceutical carrier, and the molecule's biological activity.

Selection of a suitable pharmaceutical preparation depends upon the method of administration chosen. For example, the molecules of the invention may be administered by direct injection into any cancerous tissue or into the area surrounding the cancer. In this instance, a pharmaceutical preparation comprises the molecules dispersed in a medium that is compatible with the cancerous tissue.

Molecules of the instant invention may also be administered parenterally by intravenous injection into the blood stream, or by subcutaneous, intramuscular, intrathecal, or intraperitoneal injection. Pharmaceutical preparations for parenteral injection are known in the art. If parenteral injection is selected as a method for administering the molecules, steps should be taken to ensure that sufficient amounts of the molecules reach their target cells to exert a biological effect. The lipophilicity of the molecules, or the pharmaceutical preparation in which they are delivered, may have to be increased so that the molecules can arrive at their target locations. Methods for increasing the lipophilicity of a molecule are known in the art.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral, topical, or parenteral. In preparing the molecule in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. Dosage units may be proportionately increased or decreased based on the weight of the patient. Appropriate concentrations for alleviation of a particular pathological condition may be determined by dosage concentration curve calculations, as known in the art. The appropriate dosage unit for the administration of the molecules of the instant invention may be determined by evaluating the toxicity of the molecules in animal models. Various concentrations of pharmaceutical preparations may be administered to mice with transplanted human tumors, and the minimal and maximal dosages may be determined based on the results of significant reduction of tumor size and side effects as a result of the treatment. Appropriate dosage unit may also be determined by assessing the efficacy of the treatment in combination with other standard chemotherapies. The dosage units of the molecules may be determined individually or in combination with each chemotherapy according to greater shrinkage and/or reduced growth rate of tumors.

The pharmaceutical preparation comprising the molecules of the instant invention may be administered at appropriate intervals, for example, at least twice a day or more until the pathological symptoms are reduced or alleviated, after which the dosage may be reduced to a maintenance level. The appropriate interval in a particular case would normally depend on the condition of the patient.

According to another aspect of the instant invention, methods for determining whether a cancer is susceptible to the CD19-PI3K inhibitors of the instant invention are provided. In a particular embodiment, the method comprises determining the presence of a gain-of-function mutation in Myc (e.g., at amino acid threonine 58) in a cell (e.g., a cancer cell or B-cell obtained from a subject (e.g., as part of a biological sample obtained from the subject)), wherein the presence of the gain-of-function mutation in Myc is indicative that the cell is resistant to PI3K inhibitors and CD19-PI3K inhibitors. In another embodiment, the method comprises determining the presence of a loss-of-function mutation in Pax5 (e.g., Mullighan et al. (2007) Nature 446:758-761) in a cell, wherein the presence of the loss-of-function mutation in Pax5 is indicative that the cell is resistant to PI3K inhibitors and CD19-PI3K inhibitors. In yet another embodiment, the method comprises determining the level of CD19 in a cell, wherein the presence of increased levels of CD19 compared to wild-type or normal B-cells is indicative that the cell is resistant to CD19-PI3K inhibitors.

DEFINITIONS

The following definitions are provided to facilitate an understanding of the present invention:

The singular forms "a," "an," and "the" include plural referents unless the context clearly dictates otherwise.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween® 80, Polysorbate 80), emulsifier, buffer (e.g., Tris HCl, acetate, phosphate), antimicrobial, bulking substance (e.g., lactose, mannitol), excipient, auxilliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions are preferably employed as carriers, particularly for injectable solutions. Suitable pharmaceutical carriers are described in Remington: The Science and Practice of Pharmacy, 21st Edition, (Lippincott, Williams and Wilkins; 2005); Liberman, et al., Eds., Pharmaceutical Dosage Forms, Marcel Decker, New York, N.Y., 1980; and Rowe, et al., Eds., Handbook of Pharmaceutical Excipients (6th Ed.), Pharmaceutical Pr, 2009.

The term "treat" as used herein refers to any type of treatment that imparts a benefit to a patient afflicted with a disease, including improvement in the condition of the patient (e.g., in one or more symptoms), delay in the progression of the condition, etc.

As used herein, the term "prevent" refers to the prophylactic treatment of a subject who is at risk of developing a condition (e.g., cancer) resulting in a decrease in the probability that the subject will develop the condition.

A "therapeutically effective amount" of a compound or a pharmaceutical composition refers to an amount effective to prevent, inhibit, or treat a particular disorder or disease and/or the symptoms thereof.

As used herein, the term "subject" refers to an animal, particularly a mammal, particularly a human.

As used herein, the term "small molecule" refers to a substance or compound that has a relatively low molecular weight (e.g., less than 4,000, particularly less than 2,000). Typically, small molecules are organic, but are not proteins, polypeptides, or nucleic acids, though they may be amino acids or dipeptides.

An "antibody" or "antibody molecule" is any immunoglobulin, including antibodies and fragments thereof, that binds to a specific antigen. As used herein, antibody or antibody molecule contemplates intact immunoglobulin molecules, immunologically active portions of an immunoglobulin molecule, and fusions of immunologically active portions of an immunoglobulin molecule. The term includes polyclonal, monoclonal, chimeric, single domain (Dab) and bispecific antibodies. As used herein, antibody or antibody molecule contemplates recombinantly generated intact immunoglobulin molecules and molecules comprising immunologically active portions of an immunoglobulin molecule such as, without limitation: Fab, Fab', F(ab')$_2$, F(v), scFv, scFv$_2$, scFv-Fc, minibody, diabody, tetrabody, and single variable domain (e.g., variable heavy domain, variable light domain).

As used herein, the term "immunologically specific" refers to proteins/polypeptides, particularly antibodies, that bind to one or more epitopes of a protein or compound of interest, but which do not substantially recognize and bind other molecules in a sample containing a mixed population of antigenic biological molecules.

The phrase "small, interfering RNA (siRNA)" refers to a short (typically less than 30 nucleotides long, particularly 12-30 or 20-25 nucleotides in length) double stranded RNA molecule. Typically, the siRNA modulates the expression of a gene to which the siRNA is targeted. Methods of identifying and synthesizing siRNA molecules are known in the art (see, e.g., Ausubel et al. (2006) Current Protocols in Molecular Biology, John Wiley and Sons, Inc). As used herein, the term siRNA may include short hairpin RNA molecules (shRNA). Typically, shRNA molecules consist of short complementary sequences separated by a small loop sequence wherein one of the sequences is complimentary to the gene target. shRNA molecules are typically processed into an siRNA within the cell by endonucleases. Exemplary modifications to siRNA molecules are provided in U.S. Application Publication No. 20050032733. Expression vectors for the expression of siRNA molecules preferably employ a strong promoter which may be constitutive or regulated. Such promoters are well known in the art and include, but are not limited to, RNA polymerase II promoters, the T7 RNA polymerase promoter, and the RNA polymerase III promoters U6 and H1 (see, e.g., Myslinski et al. (2001) Nucl. Acids Res., 29:2502 09).

"Antisense nucleic acid molecules" or "antisense oligonucleotides" include nucleic acid molecules (e.g., single stranded molecules) which are targeted (complementary) to a chosen sequence (e.g., to translation initiation sites and/or splice sites) to inhibit the expression of a protein of interest. Such antisense molecules are typically between about 15 and about 50 nucleotides in length, more particularly between about 15 and about 30 nucleotides, and often span the translational start site of mRNA molecules. Antisense constructs may also be generated which contain the entire sequence of the target nucleic acid molecule in reverse orientation. Antisense oligonucleotides targeted to any known nucleotide sequence can be prepared by oligonucleotide synthesis according to standard methods.

The phrase "solid support" refers to any solid surface including, without limitation, any chip (for example, silica-based, glass, or gold chip), glass slide, membrane, plate, bead, solid particle (for example, agarose, sepharose, polystyrene or magnetic bead), column (or column material), test tube, or microtiter dish.

The following examples provide illustrative methods of practicing the instant invention, and are not intended to limit the scope of the invention in any way.

Example 1

Material and Methods

Cell Cultures and Treatment with PI3K Inhibitor

Myc5 and Myc5-M5 murine B-lymphoma cells were cultured as described (Cozma et al. (2007) J. Clin. Inv., 117:2602-2610; Yu et al. (2003) Blood 101:1950-1955;

Johnson et al. (2004) Nat. Immunol., 5:853-861; Chung et al. (2008) Cancer Biol. Ther., 7:1758-1764). Human B-lymphoblastic cell line P493-6 carries an inducible c-Myc repression system where c-Myc transcription is by the synthetic tetO7-TP promoter (Pajic et al. (2000) Int. J. Cancer 87:787-793). They were cultured in RPMI-1640 (BioWhittaker) supplemented with 10% heat-inactivated tet-free FBS (Clontech), 100 U/mL penicillin, and 100 ng/mL streptomycin (Gibco). c-Myc expression in P493-6 was inhibited upon addition of doxycycline. In some experiments, P493-6 was treated with the PI3K inhibitor LY294002 (#9901; Cell Signaling) at 10 μM concentration.

Primary B Cells Cultures

Whole spleens were obtained from C57BL/6 female mice 8-12 weeks of age and gently grinded with a round-ended plunger of a 1 ml-syringe followed by passing the cells over a 70 micron-cell strainer. Red blood cells from the splenocytes were lysed with red cell lysis buffer (Sigma) for 2 minutes at room temperature (RT). Cells were then counted and seeded at $1 \times 10^6$/ml in complete RPMI medium supplemented with 50 μM β-ME. After culturing for 2 hours in an incubator set at 37° C. with 5% $CO_2$, floating cells were harvested. They were seeded at $1 \times 10^6$ cells/ml with the aforementioned medium supplemented with LPS (stock concentration 10 ng/ml) used at 1:1000 dilution. Splenocytes were cultured for 3 days with LPS. Medium and LPS were replenished every day and cells were also counted very day to check for growth. By Day 3, cells were >90% $CD19^+B220^+$ accessed by flow cytometry. Bone marrow from female WT or CD19 knockout mice (C57BL/6 background; Rickert et al. (1995) Nature 376:352-355) 8-12 weeks of age were obtained by flushing the femurs and tibias with complete DMEM. Red blood cells from the bone marrow were lyzed with red cell lysis buffer (Sigma) for 2 minutes at RT. Cells were then counted and seeded at $0.5 \times 10^6$ cells/35 mm dish in MethoCult™ medium containing IL-7. Day 9 cells were >90% $CD19^+B220^+$ accessed by flow cytometry. BD Pharmingen antibodies used for flow cytometry were PE Rat anti-mouse CD19 (cat#557399;), FITC Rat anti-mouse CD45R/B220 (cat#553088). Control antibodies include FITC rat $IgG_a$ (cat#553929) and PE rat $IgG_a$ (cat#553930).

Retroviral Production and Transduction

To over-express Pax5 or CD19 in Myc5 cells, cells were transduced with retroviral construct Pax5-MIGR1 (Cozma et al. (2007) J. Clin. Inv., 117:2602-2610; Yu et al. (2003) Blood 101:1950-1955) or CD19-pMx-ires-GFP (Dr. Tomohiro Kurosaki at RIKEN Research Institute, Yokohama, Japan). Transduction with empty vector served as control. To elucidate the effect of ITAM mediated signaling in Myc5 cells, cells were transduced with retrovirus MIGR1 encoding either the WT or the mutant form of ITAM, where both tyrosines Yxx(L/I)x6-8Yxx(L/I), were replaced with alanine. ITAM constructs were from Genentech (San Francisco, Calif.). Transduced cells were analyzed for GFP expression 24 hours post-transduction to determine transfection efficiency. Transduced cells were also sorted for GFP expression using identical gates based on GFP expression and collected for protein analysis. To over-express the constitutively active form of AKT, retroviral construct pLNCX1 encoding HA tagged-myristolated AKT1 or AKT2 were transduced into Myc5 cells (Dr. Morris Birnbaum, University of Pennsylvania Philadelphia Pa.). Transduced cells were selected with G418 (Sigma) for 2 weeks and over-expression of retroviral constructs was assayed through HA expression by Western blotting. cDNAs of murine PTEN, WT human Myc and the T58A Myc variant (Dr. Michael Cole, Dartmouth Medical School, Hanover, N.H.) were cloned into the retroviral vector MSCV-ires-NGFR. Transfection efficiency were determined by flow cytometry with either isotype control anti-body PE mouse IgG1 (555749; BD Pharmingen™) or PE mouse anti-human CD271/NGFR (560927; BD Pharmingen™) to detect the expression of NGFR on the cell surface. All retroviruses were generated using transfection with Lipofectamine™ 2000 (Invitrogen) into GP293 cells. Infections were carried over the course of 30 hours in the presence of polybrene (4 μg/ml).

Western Blotting and Immunoprecipitations

Total cell lysates were prepared and Western blotting was performed as described (Chung et al. (2008) Cancer Biol. Ther., 7:1758-1764). Antibody against Pax5 was obtained from Dr. Michael L. Atchison, University of Pennsylvania, Philadelphia, Pa. Other primary antibodies used in this study include anti-CD19 (#3574; Cell Signaling), anti-PAN AKT (#4691; Cell Signaling), anti-phospho-AKT (ser473; #4060; Cell Signaling), anti-Total GSK3β (#9315; Cell Signaling), anti-phospho-GSK3β (ser9, #9336; Cell Signaling), anti-Total c-Myc (OP-10; Calbiochem) for detecting retroviral c-Myc in P493 and Myc5 cells, anti-Total c-Myc (#5605; Cell signaling) for detecting c-Myc in splenic B and bone marrow derived B cells, anti-p-c-Myc Thr58 (A00242; Genscript), anti-p-c-Myc Ser62 (ab78318; abcam), anti-Total Lyn (#2732; Cell Signaling), anti-phospho-Lyn (tyr396; ab40660; Abcam), rabbit anti-HA clone (Cat#H6908; Sigma), anti-CD22 (sc-7932; Santa Cruz), and anti-β-Actin (A3853; Sigma). For immunoprecipitations HA-tagged WT or mutant ITAM transduced Myc5 cells were harvested by washing once in cold PBS, followed by lysis in cold passive lysis buffer containing protease and phosphatase inhibitors. HA tagged-ITAMs were immunoprecipitated from equal number of cells for each sample at a cell-to-volume ratio of $1 \times 10^6$ cells/ml of passive lysis buffer using a 1:1000 dilution of the mouse monoclonal anti-HA clone 12CA5 (Cat#11583 816 001; Roche). Antibody incubation was performed at 4° C. for 14-18 hr followed by immunoprecipitation with Protein-A beads (Invitrogen) and washing with cold passive lysis buffer containing protease and phosphatase inhibitors.

Cycloheximide Experiment

Myc5 stably transduced with either Pax5 or CD19 retroviral construct were seeded at $1 \times 10^6$/ml in 50 ml conical tubes received cycloheximide (Sigma) treatment at 1 μg/ml, while stimulation with 95% ethanol (sigma) served as control. Cells were stimulated for 0, 7.5, 15, and 30 minutes and harvest by spinning at 1700 rpm for 1 minute followed by immediate lysis in protein lysis buffer (Bio-rad). Protein samples were resolved on 10% SDS-PAGE for Western blot analysis. c-Myc protein levels were quantified by densitometry using ImageJ 1.43 (National Institutes of Health) with quantitated values normalized to β-actin.

Pulse Chase experiment

Myc5 stably transduced with either Pax5 or CD19 retroviral construct were pre-starved for methionine by replacing the culture medium with RPMI lacking L-methionine for 1 hour. Cells were labeled in vivo with $^{35}S$-methionine using 0.2 mCi/ml at the density of $10^7$ cells/ml for 30 minutes. After labeling, cells were immediately washed once with RPMI containing 5 mM L-methionine and then incubated in the same media for the indicated chase times. Cells were harvested and c-Myc proteins were immunoprecipitated. Labeled c-Myc was visualized by autoradiography and quantified using a phosphorimager.

Tumor Load Studies

All animal experiments have been reviewed and approved by Children's Hospital of Philadelphia Institutional Animal Care and Use Committee (IACUC) (protocol number 2009-12-902).

For in vivo experiments, $1.5 \times 10^7$ Myc5-M5 cells stably transduced with empty retroviral vector, pMx-ires-GFP or retroviral vector encoding CD19. Transduced cells sorted for the highest GFP+ expression were injected subcutaneously into SCID mice (National Cancer Institute). Tumor size was measured every other day using caliper, and tumor weights were recorded on the day of tumor excision. Protein lysates were obtained from tumors for Western blot analysis by lysing tumors at a ratio of 40 mg of tumor/ml of lysis buffer. Tumors from Myc5-M5 cells infected with retrovirus encoding Pax5ER$^{TAM}$ (+4OHT) or its control vector (+4OHT) were obtained (Cozma et al. (2007) J. Clin. Inv., 117:2602-2610) and protein lysates were obtained for Western blot analysis.

Proliferation Assay

Proliferation of Myc5-M5 CD19 transduced cells in vitro were determined using cell proliferation reagent WST-1 (Roche Molecular Biochemicals). Cells were seeded at $1 \times 10^3$/well in 100 µl of culture medium were incubated for a total of 72 hours. Proliferation status was determined every 24 hours by incubating with 10 µl of the cell proliferation reagent WST-1 for 4 hours. The absorbance of the treated samples in triplicates were measured against a blank control was measured at 440 nM using a Synergy™ 2 microplate reader (BioTek Instruments).

siRNA Knockdown Experiments

P493-6 were treated with the double-stranded ON-TARGET Plus™ SMARTpool® siRNA either against human Pax5 (L-012241-00; Dharmacon), human total GSK3β (L-003010-00; Dharmacon) or human CD19 (sc-29968; Santa Cruz). A non-targeting pool of siRNA (D-001810-10) was used as negative control (Dharmacon) for siRNA experiments. ON-TARGET sets of 4 individual siRNAs against human Pax5, CD19 or GSK3β were used. siRNA were electroporated into P493-6 cells with Amaxa® Nucleofactor® according to the manufacturer's instructions (Lonza AG). Efficiency of siRNA delivery was confirmed with a non-specific double-stranded BLOCK-iT™ fluorescent oligo (#2013; Invitrogen). The effectiveness of silencing was confirmed by Western blotting. Myc5 stably transduced with CD19 retroviral construct or the control vector were electroporated with 10 nM of control or anti-human Myc siRNA (L-003282; Dharmacon). Cells were harvested 24 hours post electroporation and accounted for cell growth.

Real-Time q-PCR

Real-time q-PCR was performed with Applied Biosystems® 7500 system. Primer sequences used for amplifications in murine Myc5_M5 derived tumors were: CDK4 sense 5'-caatgttgtacggctgatgg-3' (SEQ ID NO: 1); CDK4 anti-sense 5'-caggccgcttagaaactgac-3' (SEQ ID NO: 2); ODC1 sense 5'-gtggcaactcatgaagcaga-3' (SEQ ID NO: 3); ODC1 anti-sense 5'-tgcaggcaagagctacaaga-3' (SEQ ID NO: 4); LDHA sense 5'-tccgttacctgatgggagag-3' (SEQ ID NO: 5); LDHA anti-sense 5'-gtaggcactgtccaccacct-3' (SEQ ID NO: 6).

Statistical Analysis of Cell and Tumor Growth

Cell proliferation study was performed in triplicates. CD19 tumor study was performed with 5 mice per group. Statistical significance was assessed by a one-tailed unpaired Student's t-test.

Gene Set Enrichment and Survival Analyses

Data from the Hummel and Lenz studies were downloaded from the Gene Expression Omnibus gateway (www.ncbi.nlm.nih.gov/geo/) using GEO accession numbers GSE4475 and GSE10846, respectively. Patients from the Hummel study were initially sorted into Ig-MYC translocation-positive and -negative. The translocation-negative neoplasms were further sorted into CD19 high, intermediate, or low. Gene Set Enrichment Analysis was performed comparing the expression data from CD19$^{HIGH}$ and CD19$^{LOW}$ tumors. The data from Lenz and Hummel studies were also used to evaluate the effect of CD19 and MYC expression on patient survival as the two studies had similar design and could be combined. Using the pooled data, the tertiles of the normalized CD19 and MYC values were calculated and the patients were categorized into three groups: CD19 (or MYC) low, CD19 (or MYC) intermediate, and CD19 (or MYC) high. The Kaplan-Meier (KM) curves of the CD19 (or MYC) high group and CD19 (or MYC) low group were compared.

Statistics Overview

For the survival analysis, a stratified log-rank test was conducted, testing the CD19 effect stratifying on the study number (Kalbfleisch et al. (2002) The statistical analysis of failure time data. John Wiley & Sons, Inc. New York) to account for the potential difference in the two studies. A two-sided P value of <0.05 was considered statistically significant and SAS 9.2 was used to perform the analysis. For GSEA, a nominal P value of <0.05 in combination with an FDR q-value <0.25 was considered statistically significant.

Results

Pax5 Sustains c-Myc Protein Levels

It was first determined whether shutting down Myc expression would compromise Pax5 protein levels. P493-6 cells were treated with doxycycline (Dox) for 2-12 hours. While Myc protein levels decreased sharply 2 hours after Dox treatment, there were no appreciable changes in Pax5 levels, as judged by Western blotting (FIG. 1A, left panels). Even after prolonged exposure to Dox (24-48 hours) Pax5 expression levels were unaffected (FIG. 1A, right panels). To determine whether changes in Pax5 expression affect Myc protein levels, Pax5 expression was restored in MYC5 cells using the Pax5-encoding retroviral vector (MIGR1). Cells lysates were harvested 24 and 48 hours post infection and analyzed by Western blotting. At both time points, a clear increase in Myc levels was observed (FIG. 1B). To determine if Myc levels are induced by Pax5 in vivo, Myc5 tumors reconstituted with conditionally active Pax5-estrogen receptor (ER) fusion were analyzed (Cozma et al. (2007) J. Clin. Inv., 117:2602-2610). To ensure Pax5 activity, all tumor-bearing mice had been treated with the ER ligand 4-hydroxytamoxifen (4-OHT). In these specimens, too, there was a strong positive correlation between Myc and Pax5ER levels (FIG. 1C). In contrast, CD22 levels were down-regulated by Pax5.

To reproduce this result in a different cell system using a loss-of-function approach, Pax5 was knocked down with siRNA in P493-6 cells. To optimize transfection conditions, FITC-labeled, double-stranded RNA duplexes were electroporated separately into P493-6 cells, and flow cytometry was performed to determine the efficiency of siRNA delivery. At 0.1 µM and 1 µM, transfection efficiency ranged between 62 and 96% (FIG. 2A). Then increasing amounts of α-Pax5 SMARTpool® siRNA (10 nM, 0.1 µM and 1 µM) were introduced into P493-6 cells, and protein lysates were harvested 24 hours post electroporation for Western blot analysis. A sequence-specific, dosage-dependent decrease in Pax5 protein levels was observed, which led to a commensurate decrease in CD19, a direct Pax5 target, with maximum inhibition of both proteins achieved at 1 µM (FIG. 2B). To rule out off-target effects, 4 individual siRNAs comprising the SmartPool® were also analyzed. As expected, 3 out of 4 siRNAs inhibited Pax5 expression, and all three also caused a reproducible reduction in Myc levels (FIG. 1D). Next, the cells were treated with 1 µM of α-Pax5 siRNA and Myc levels were assessed 24 hours and 48 hours post electroporation. While no changes in Myc levels were apparent at 24 hours, they were appreciably reduced after 48 hours (FIG. 1E). This result indicated an indirect mechanism of regulation, presumably mediated by Pax5 targets.

CD19 but not B-Cell Receptor Signaling Increases c-Myc Protein Stability

Due to the absence of Pax5, Myc5 cells do not express Pax5 target genes, most notably CD79a (Ig-α). It is, however, robustly induced upon Pax5 re-expression (Cozma et al. (2007) J. Clin. Inv., 117:2602-2610) and can form a complex with constitutively expressed CD79b (Ig-β), resulting in phosphorylation of their ITAM motifs and BCR signaling. To determine if this sequence of events increases Myc levels, Myc5 cells transduced with the MIGR1 retrovirus encoding the HA-tagged ITAM of Ig-α/β in either constitutively active or mutant configuration were used, where both tyrosines are replaced with alanines (Grande et al. (2006) Oncogene 25:2748-2757). Infection efficiency was determined by flow cytometry and transduced cells were confirmed to be >97% GFP+. Protein lysates from MYC5-ITAMwt and MYC5-ITAMmut cells were first subjected to immunoprecipitation with a mouse anti-HA antibody. Then immunoprecipitates were immunoblotted for the Src family kinase Lyn, which binds specifically to the ITAM of Ig-α in B cells (Clark et al. (1992) Science 258:123-126). Rabbit anti-HA antibody-reactive ITAM was used as a loading control. As anticipated, overexpression of wild-type ITAM led to an increase in Lyn binding compared to parental and ITAMmut-transduced cells (FIG. 3A, top panel). Additionally, the amount of ITAM-bound Lyn activated via phosphorylation on $Tyr^{396}$ was also increased in ITAMwt cells. Of note, while ITAMmut induced some phospho-Lyn recruitment, it was not as robust as recruitment of Lyn by ITAMwt, attesting to the functionality of the ITAM construct (FIG. 3A, middle panel). Still, there was no change in Myc protein levels (FIG. 3A, bottom panel), indicating that activation of ITAM, a critical component of the BCR pathway, is insufficient to boost Myc protein expression.

Another major target of Pax5 is CD19 (Nutt et al. (1998) EMBO J. 17:2319-2333; Kozmik et al. (1992) Mol. Cell Biol., 12:2662-2672). Although CD19 is thought to function in the context of BCR, it might have BCR-independent functions, e.g., regulation of Myc. Thus, Ig-α-negative Myc5 cells were transduced with a CD19 retrovirus and measured steady-state Myc levels. Surprisingly, Myc expression was increased several-fold (FIG. 3B). To reproduce this result in a different cell system using the loss-of-function approach, CD19 was knocked down in P493-6 cells using SMARTpool® siRNA. Despite only partial knockdown of CD19, Myc levels were appreciably and consistently reduced while Pax5 levels were unaffected (FIG. 2C). Individual siRNAs comprising the SMARTpool® were also analyzed. The oligonucleotide responsible for most robust downregulation of CD19 also down-regulated Myc in sequence-specific and dose-dependent manners (FIG. 3C). Finally, Myc levels were measured in bone marrow-derived B-cells from CD19-deficient mice (Rickert et al. (1995) Nature 376:352-355). To this end, short-term cultures of primary B-cells were established. In these cultures, over 95% of cells were of B-cell lineage, as confirmed by B220 positivity (FIG. 4A). Once again, CD19-deficient B-cells contained lower Myc levels than their CD19-sufficient counterparts (FIG. 3D). Of note, in the three models tested (MYC5, P493-6, and primary murine B-cells), Myc expression was driven by three different regulatory elements (retroviral LTR, CMV IE region, and the endogenous myc gene promoter, respectively). Thus, the uniform down-regulation of Myc upon CD19 silencing indicated promoter-independent, post-transcriptional regulation.

Myc protein half-life was then measured in parental versus Pax5- and CD19-transduced Myc5 cells. For this experiment, CD19-positive cells were additionally fractionated into $CD19^{low}$ and $CD19^{high}$ subpopulations. The levels of CD19 overexpression in these cultures were 2.5- and 4.0-fold, respectively, compared to Pax5-driven expression levels (see mean fluorescent intensities in FIG. 3E). These calculations were confirmed by Western blotting. Nevertheless, Myc levels were comparable between $CD19^{low}$ and $CD19^{high}$ cultures, suggesting that 4-fold CD19 overexpression of CD19 is not required for Myc activation (FIG. 3F).

Then Pax5- and CD19-reconstituted lines were treated with the protein synthesis inhibitor cycloheximide (CHX; Schneider-Poetsch et al. (2010) Nat. Chem. Biol., 6:209-217) and steady-state Myc levels were measured by Western blotting. CHX treatment over the course of 30 minutes had no observable effects on retrovirally transduced-Pax5 or CD19 proteins expression, but Myc levels were clearly down-regulated (FIG. 3G). However, while in vector-transduced Myc5 cells the half-life of Myc was ~17 minutes, in cells transduced with Pax5 or CD19 Myc half-life was strongly increased, to ~90 and ~40 minutes, respectively (FIG. 3G, bottom panels).

Cycloheximide treatment has the potential to indirectly inhibit gene expression through changes in mRNA stability or protein translation. Thus, the half-life of Myc was also measured using pulse-labeling followed by chase and radio-immunoprecipitation. Fully consistent with the results of the CHX experiment, in parental cells Myc was barely detectable after 30 minutes of chase but was strongly stabilized in the presence of either Pax5 or CD19 (FIG. 3H). Thus, these two proteins are indeed positive post-transcriptional regulators of Myc protein levels.

BCR-Independent AKT Activation is Necessary and Sufficient for Myc Induction by CD19

One of the known functions of CD19 signaling is the recruitment and activation of PI3K and ensuing activation of Akt, all in the context of BCR signaling (Tuveson et al. (1993) Science 260:986-989; Buhl et al. (1999) J. Immunol., 162:4438-4446; Otero et al. (2001) J. Biol. Chem., 276:1474-1478; Fujimoto et al. (2002) J. Immunol., 168:5465-5476; Aiba et al. (2008) Blood 111:1497-1503; Gold et al. (2000) Immunol. Rev., 176:47-68). To determine whether Akt activation accompanies the stabilization of Myc by CD19, P493-6 cells were electroporated with anti-CD19 siRNA and expression levels of the Akt signaling components were assessed. As shown in FIG. 5A, CD19 knockdown decreased not only Myc protein levels but also that of phosphoserine-473 in Akt and phosphoserine-9 in Akt's target GSK3β. Total Akt and GSK3β levels were unchanged. To determine whether Akt phosphorylation was necessary for Myc stabilization, P493-6 cells were treated with the PI3K inhibitor LY294002. 1 hour LY294002 treatment resulted in decreased pAkt and pGSK3β levels as well as decreased Myc levels (FIG. 5B). Since a reduction in Myc levels was relatively modest, this experiment was repeated in splenic B-cells and analyzed for purity using flow cytometry (FIG. 4B). These short-term cultures responded to LY294002 very robustly, as evidenced by very low pAkt and pGSK3β levels and sharply down-regulated Myc (FIG. 5C).

To further establish the role of Akt in Myc induction, Myc5 cells were transduced with retroviruses encoding constitutively active Akt1 and 2. In both cases, especially in Akt2-transduced cells, a commensurate increase in inhibitory GSK3β phosphorylation and Myc steady state levels was observed (FIG. 5D). In addition to being an Akt target, GSK3β negatively regulates Myc levels by phosphorylating Thr-58, provided that Ser-62 is already phosphorylated by another kinase (Hann, S. R. (2006) Semin. Cancer Biol., 16:288-302; Sears, R. C. (2004) Cell Cycle 3:1133-1137). This allows binding of the Fbw7 ubiquitin ligase which contributes to Myc degradation (Welcker et al. (2004) Proc. Natl. Acad. Sci., 101:9085-9090). Thus, the same protein lysates were probed with antibodies against Myc residues Thr-58 and Ser-62. While Thr-58 phosphorylation was decreased in Akt-expressing cells, GSK3β-independent Ser-62 phosphorylation was increased (Lutterbach et al. (1994) Mol. Cell Biol., 14:5510-5522).

To determine whether GSK3β controls Myc protein levels, increasing concentrations of anti-GSK33 siRNA (10 nM, 0.1 µM and 1 µM) were electroporated into P493-6 cells. As evidenced by data in FIG. 5E, GSK3β knock-down led to robust upregulation of Myc, attesting to the key role of PI3K-Akt-GSK3β pathway in regulating Myc protein output in B-cells. Similar effects were observed with individual siRNA comprising the SMARTpool® (FIG. 2D). To further validate this finding, the effects of mutating the GSK3β consensus site in Myc (Thr58Ala) were analyzed. GFP- and Pax5-overexpressing MYC5 cells were additionally transduced with either wild-type or T58A Myc constructs. Pax5 increased expression levels of both endogenous and retrovirally encoded wild-type Myc but not the T58A variant (FIG. 5F).

Finally, it was determined whether the Akt-GSK3β axis is necessary for Myc activation by CD19 in BCR-negative cells. The analysis of control vector (MSCV-ires-NGFR)- and CD19-transduced Myc5 cells revealed the same increase in activating phosphorylation of Akt and inhibitory phosphorylation of GSK3β as in BCR-sufficient B-cells (FIG. 5G, left two columns). Then the same experiment was repeated with cells engineered to overexpress PTEN, the key negative regulator of the PI3K pathway. As expected, PTEN completely abolished Akt activation by CD19 and also prevented Myc upregulation (FIG. 5G, right two columns), establishing a causal relationship between these two phenomena.

The CD19-Myc Axis Promotes Cell Expansion In Vitro and In Vivo

Given the prominent role of Myc in cell division, it was determined whether CD19 promotes cells growth in a Myc-dependent manner. To this end, parental and CD19-expressing MYC5 cells were treated with siRNA against Myc, bringing down both basal and CD19-induced Myc levels. The effects of CD19 on cell growth in the presence of α-Myc siRNA were much smaller than those seen in the presence of control siRNA (FIG. 6A). However, in the presence of CD19, anti-Myc siRNA was not as effective as in control cells in reducing Myc levels (FIG. 6B), complicating interpretation of the results. Thus, the growth rates of Pax5-, CD19-, and Myc-transduced MYC5 cells were also compared (from FIGS. 3F and 5F, respectively). Pax5-transduced cells grew appreciably faster when compared to cells transduced with CD19 or Myc (FIG. 6C), perhaps because in addition to CD19 Pax5 reactivates Igα and growth-promoting BCR signaling (Cozma et al. (2007) J. Clin. Inv., 117:2602-2610). However, CD19- and Myc-transduced cells proliferated at approximately the same rates suggesting that CD19-induced proliferation doesn't have a significant Myc-independent component (FIG. 6C).

To determine whether CD19 also promotes cell growth in vivo, the MYC5 M5 subclone, which does not reactivate Pax5 and CD19 when injected into mice, were utilized (Cozma et al. (2007) J. Clin. Inv., 117:2602-2610; Yu et al. (2003) Blood 101:1950-1955). Reconstitution of Myc5-M5 cells with CD19 was performed as described for parental Myc5 cells, using sorting for GFP (FIG. 7A). MYC5-M5/CD19 cells retained their quasi-myeloid lineage in that they were still positive for Mac1 and negative for B220 (FIG. 7B). They also robustly upregulated phospho-Akt and Myc (FIG. 6D). To determine whether Myc target genes responsible for cell cycle progression are upregulated in CD19-reconstituted cells, mRNA levels of three key Myc-activated genes, ODC1, LDHA, and CDK4, were measured (Bello-Fernandez et al. (1993) Proc. Natl. Acad. Sci., 90:7804-7808; Schuhmacher et al. (2001) Nucl. Acids Res., 29:397-406; Elkon et al. (2004) Nucl. Acids Res., 32:4955-4961; Hermeking et al. (2000) Proc. Natl. Acad. Sci., 97:2229-2234). In all three cases, elevated mRNA levels in CD19-sufficient vs. CD19-deficient cultures were observed (FIG. 6E). Also, it was demonstrated that widespread downregulation of microRNAs by Myc contributes to neoplastic growth (Chang et al. (2008) Nat. Genet., 40:43-50). Thus, levels of five key Myc-repressed microRNAs in CD19-negative and -reconstituted Myc5 cells lines were compared. For all five growth-suppressive microRNA tested (miR-16, miR-34a, miR-150, miR-195, and let-7e), decreased levels in CD19-reconstituted cells were observed (FIG. 7C).

Control and CD19-reconstituted MYC5-M5 cells were injected into immunocompromised mice. The resultant tumors were analyzed for the components of the CD19-Myc axis. Increased Myc levels were accompanied by increased levels of phospho-Akt and phospho-GSK3β (FIG. 6F), while tumor cells expressing mutant CD19 failed to activate Akt and upregulate Myc protein expression, further stressing the importance of this pathway for Myc-dependent neoplastic growth. Of note, CD19-reconstituted cells grew much faster and ultimately formed much larger neoplasms (FIG. 6G) than control GFP-only cells. This leads to a molecular model wherein CD19 control Myc levels in a manner dependent of PI3K but not the BCR (FIG. 8A).

Finally, it was determined whether CD19 contributes to Myc function in human B-lymphomas. It was hypothesized that tumors exhibiting increased CD19 expression would in turn exhibit increased expression of Myc targets. To this end, the publicly available dataset corresponding to hundreds of tumor specimens profiled in the Hummel study were analyzed (Hummel et al. (2006) N. Engl. J. Med., 354:2419-2430). To avoid Burkitt's lymphoma cases that frequently harbor Thr-58 mutations (Hoang et al. (1995) Mol. Cell Biol., 15:4031-4042), 142 diffuse large B-cell lymphomas without Ig-MYC translocations were focused on. Using these filtered cases, patient samples were categorized into three groups (CD19 high, intermediate, and low) and performed Gene Set Enrichment Analysis (GSEA; Subramanian et al. (2005) Proc. Natl. Acad. Sci., 102:15545-15550) comparing $CD19^{HIGH}$ and $CD19^{LOW}$ tumors. It was observed that $CD19^{HIGH}$ tumors exhibited enrichment for the curated gene set DANG_MYC_TARGETS_UP (Zeller et al. (2003) Genome Biol., 4:R69.1-R69.10) (FIG. 8B).

This enrichment was highly significant, with the normalized enrichment score of 1.510677, p-value <0.026476579, and FDR q-value <0.17252263. Importantly, the enriched set included the three well-validated Myc targets ODC1, CDK4, and LDHA, as demonstrated in the heatmap in FIG. 8C.

Since this analysis strongly connects CD19 expression to the expression of Myc targets, it was further postulated that CD19 and Myc would have similar effects on patient survival. In addition to the Hummel analysis, the Lenz study which profiled mRNA expression in conjunction with survival data for hundreds of diffuse large B-cell lymphoma (DLBCL) patients was included (Lenz et al. (2008) N. Engl. J. Med., 359:2313-2323). In order to maintain the fidelity of each individual study while gaining statistical insight from both, the stratified log-rank test was used to determine the significance of gene expression levels for overall survival. Of note, the distribution of normalized MYC and CD19 values and the estimated KM curves of the two studies were similar, confirming the appropriateness of combining the two studies. It was first investigated how MYC levels would affect patient survival. In each study, the patients with low MYC expression values had better survival, compared to patients with high MYC values (FIG. 8D). The stratified log-rank test yielded a chi-square value of 15.17 and a p-value of <0.0001, indicating a significant negative effect of MYC on survival. It was then explored how CD19 affects patient survival. Confirming the hypothesis, CD19 expression had similar effects on patient survival as MYC expression (compare FIGS. 8D and 8E). Again, the stratified log-rank test (Kalbfleisch et al. (2002) The statistical analysis of failure time data. John Wiley & Sons, Inc. New York) yielded a chi-square value of 5.39 and a p-value of 0.0203, indicating that CD19 levels have a significant negative effect on patient survival. Thus, both the GSEA and survival analysis show that CD19 positively regulates Myc function in human B-lymphomas.

Example 2

It is well-known that in most types of B-cells CD19 functions as a co-receptor of the B-cell receptor (BCR). In order to better understand how CD19- and the BCR as a whole—affect lymphoma patient survival, two publicly available datasets were utilized. In the first study, short hairpins were used to knock down cd79a, a component of the BCR, in the HBL-1 diffuse large B-cell lymphoma (DLBCL) cell line that exhibits chronically active BCR signaling. From the mRNA profiling changes that occur during knockdown, a "BCR signature", i.e. a set of genes whose expression was dependent upon a functional BCR, was identified. A second dataset, in which 420 human DLBCL tumors were profiled, was then utilized. Each tumor was assigned a BCR signature score based on the average expression of genes in the BCR signature. Among patients with DLBCL, the activated B-cell (ABC-) subtype is considered more aggressive and patient mortality is significantly higher than observed for the germinal center B-cell (GCB-) subtype (and the less common mediastinal lymphoma). For this reason, the tumors were divided into two groups based on subtype classification. When patients with high BCR signatures were compared to patients with low BCR signatures, high BCR signature negatively affected the survival of ABC-, but not GCB-, DLBCL patients (FIGS. 9A and 9B) indicating that the pathogenesis of ABC-DLBCL depends on BCR signaling. Accordingly, targeting the BCR will provide therapeutic benefit.

The miR-17~92 microRNA cluster (Olive et al. (2010) Intl. J. Biochem. Cell Biol., 42:1348-54; Inomata et al. (2009) Blood 113:396-402) is implicated in the regulation of the BCR. It was then determined if a relationship between miR-17~92 and BCR signaling pertains to B-lymphomagenesis in humans. To this end, the BCR metagene was correlated to the expression of the miR-17~92 primary transcript mir17hg (FIG. 9D). In ABC-DLBCLs, there was a significant correlation between the BCR signature and mir17hg expression (FIG. 9D). Patients with high mir17hg expression were then compared to patients with low mir17hg expression (FIG. 9E). Despite being identified as an oncogene in humans and mice, high mir17hg expression alone did not significantly alter patient survival. To further dissect the interplay between miR-17~92 and BCR signaling on ABC-DLBCL patient survival, the patients were divided into four groups: High BCR Signature/High MIR17HG, High BCR Signature/Low MIR17HG, Low BCR Signature/High MIR17HG, and Low BCR Signature/Low MIR17HG. When mir17hg expression is low, high levels of BCR signaling (High BCR Signature/Low MIR17HG) do not affect patient survival relative to patients with low levels of BCR signaling (Low BCR Signature/Low MIR17HG) (FIG. 9G). Strikingly, however, High BCR Signature/High MIR17HG patient survival is significantly compromised compared to Low BCR Signature/High MIR17HG patients (FIG. 9F). The impact of BCR signaling on patient mortality is exacerbated by high mir17hg expression (compare FIG. 9F to 9G) even though mir17hg by itself does not affect mortality (FIG. 9E). Accordingly, miR-17~92 cooperates with BCR signaling to negatively affect ABC-DLBCL patient survival.

In order to positively regulate BCR signaling, miR-17~92 cluster members could target negative regulators of BCR signaling and these targets would act upstream of B-cell linker protein (BLNK) phosphorylation. TargetScan (www.targetscan.org/) was searched for negative regulators with predicted miR-17~92 binding sites in their 3'UTRs and cd22 and fcgr2b were identified, both of which encode immunoreceptor tyrosine inhibitory motifs (ITIMs). It was then determined whether this regulation was the result of direct targeting by miR-17~92 cluster members or an indirect effect. To probe for direct binding of miR-19a and -18a to the cd22 and fcgr2b 3'UTRs (respectively), dual luciferase sensor assays were utilized. Specifically, 100 bp fragments of each 3'UTR was cloned downstream of the renilla luciferase gene while firefly luciferase provided an internal control (FIGS. 10D-10E). In addition to fragments with wild-type 3'UTRs, constructs with mutations in the predicted seed sequences were cloned for negative controls. Each individual plasmid construct (empty vector, wild-type 3'UTR, and mutant 3'UTR) and matching miRNA mimic were co-transfected into HCT116 Dicer hypomorph cells and luciferase activity was measured 48 hours later. The cd22 and fcgr2b 3'UTRs are directly targeted by miR-19a and miR-18a (FIGS. 10D-10E). The wild-type cd22 3'UTR exhibited a 25% (statistically significant) reduction in luciferase activity compared to the mutant 3'UTR construct (FIG. 10D). In the fcgr2b experiments, transfection of miR-18a resulted in decreased luciferase activity for all constructs (FIG. 10E). However, the wild-type fcgr2b 3'UTR exhibited additional reduction in luciferase activity compared to the mutant 3'UTR construct and this difference was also significant (FIG. 10E).

In a pathway parallel to BLNK phosphorylation, BCR ligation also leads to Akt phosphorylation. miR-17~92 could increase Akt phosphorylation by inhibiting CD22 and FCGR2B, thus rendering SHIP less active. Lymphoma cells were treated with either control or miR-17~92 mimic prior to stimulation with soluble anti-IgM and cells were harvested 30 and 90 minutes after ligation (FIG. 10F). In both control and miR-17~92 mimic treated cells, increased phosphorylation of Akt was observed after BCR ligation (FIG. 10F). However, the phosphorylation increase was greater in miR-17~92 mimic treated cells suggesting that miR-17~92 mediated amplification of BCR signaling could affect multiple downstream signaling pathways (FIG. 10F). Akt1 directly inhibits glycogen synthase kinase 3β (GSK3β) through phosphorylation and further downstream, GSK3β targets Myc for degradation. Therefore, Akt phosphorylation renders GSK3b inactive and results in increased Myc levels in B-cells. Indeed, increased GSK3β phosphorylation was observed in the presence of exogenous miR-17~92 mimic (FIG. 10F). Myc was found to be more strongly upregulated in miR-17~92 treated cells (FIG. 10F). These results establish that Myc, via miR-17~92, stimulates the BCR response and participates in a feed-forward regulatory loop (see, e.g., model in FIG. 10G).

Example 3

To identify pathway(s) that could become activated following inhibition of PI3K signaling, MYC5 cells and the CD19 mutant that is unable to recruit PI3K were utilized. Interestingly, while MYC5-CD19mut neoplasms grew appreciably slower than CD19 wt, they still grew much faster than CD19-negative neoplasms (FIG. 11A, 11B). To determine what alternative growth pathway is activated by CD19mut, various arms of MAPK signaling were profiled, given their reported links to CD19. Unexpectedly, while no major changes in phosphorylation of Erk and p38 were observed, CD19mut (but not CD19 wt) strongly increased phosphorylation of the Jun kinase JNK (FIG. 11C). Similar effects were noted in CD19-sufficient B-cells treated with the PI3K inhibitor LY294002 (FIG. 11D). Provocatively, JNK is known to be activated by Src family tyrosine kinases (SFTKs), and SFTK Lyn and Fyn are activated via recruitment to plasma membrane by CD19. Consistent with this putative pathway, inhibition of SFTK using the Sugen compound SU6656 reduced phospho-JNK levels and selectively suppressed proliferation of CD19mut/PI3K-disabled cells (FIG. 11E, 11F). Moreover, CD19mut/PI3K-disabled cells preferentially phosphorylate the SFTK Lyn (FIG. 11G).

Figure 12A:
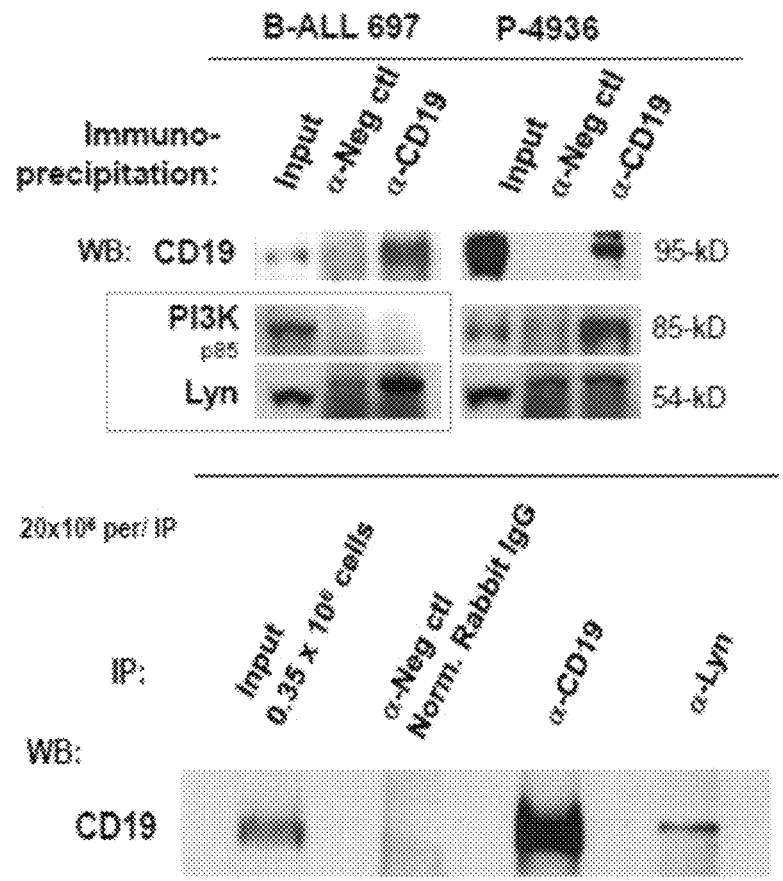

It was hypothesized that JNK is activated via CD19/Lyn-mediated signaling in the absence of PI3Krecruitment/activation. An interesting parallel between the murine Myc5 B-lymphoma system and human B-cell acute lymphoblastic leukemia (B-ALL) cells was identified. Similar to Myc5 cells, CD19+ B-ALL cells do not express the surface (s)-IgM (i.e., the BCR) and do not respond to s-IgM stimulation. Furthermore, data from immunoprecipitation experiments in B-ALL cells using an anti-CD19 antibody demonstrates that CD19 interacts with Lyn but not PI3K, while in P493-6 lymphoma cells both interactions occur (FIG. 12A, top panel). CD19 is co-immunoprecipitated in B-ALL cells when an antibody recognizing Lyn was used (FIG. 12A, bottom panel).

Figure 12B:
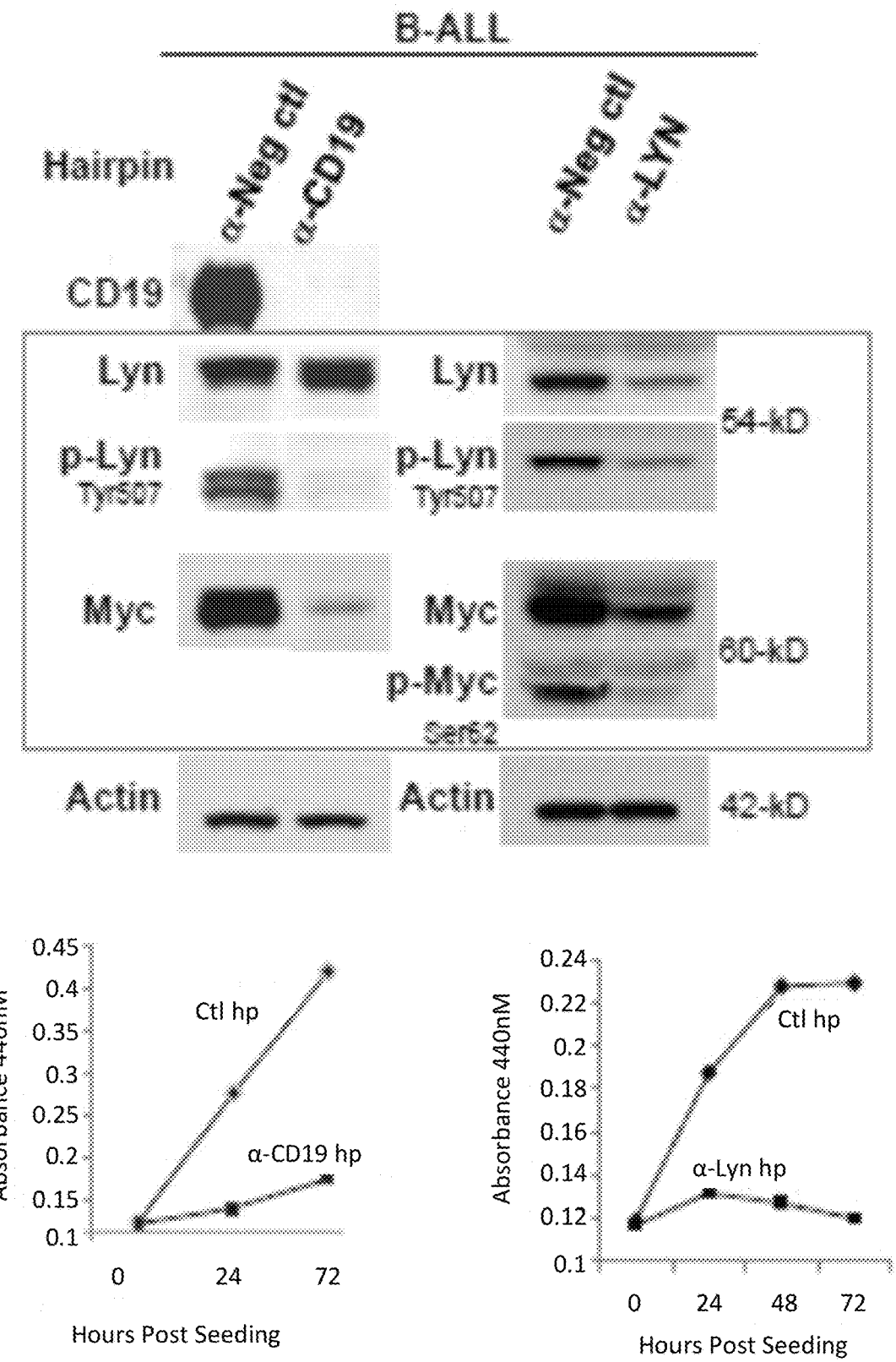
Figure 12C:
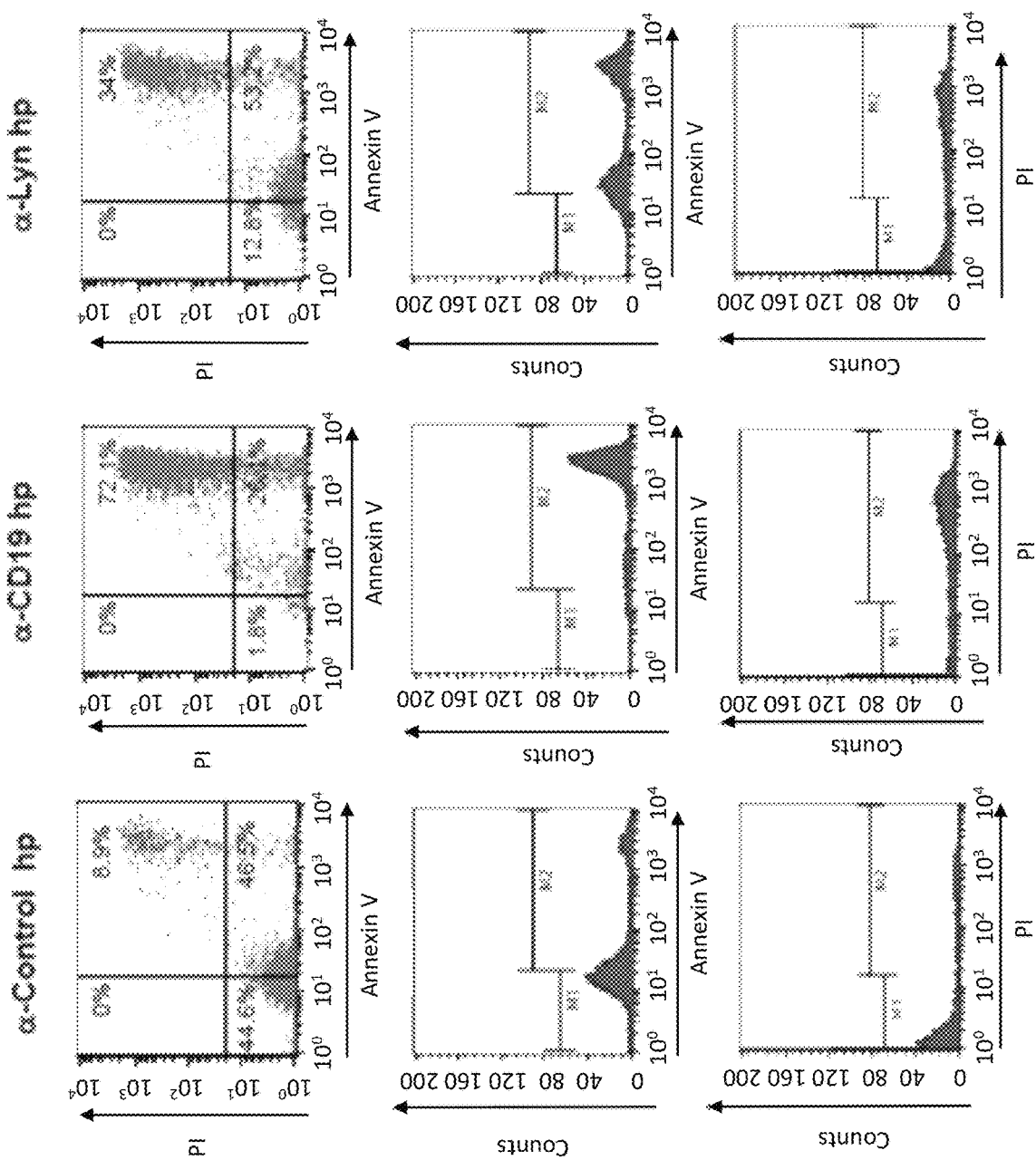

It was found that CD19 is important for the growth and survival of B-ALL cells because knock-down of CD19 using shRNA inhibited growth and triggered apoptosis in B-ALL cells (FIG. 12B, top left and bottom left panels). This impediment in growth and apoptosis following CD19 knockdown is largely explained by impaired Lyn-mediated signaling. This is because treatment with anti-Lyn hairpin also inhibits cell growth and triggered apoptosis (FIG. 12B, top right and bottom right panels). This could be further attributed to the decrease in Myc levels since treatment with either CD19 or Lyn hairpin inhibits Myc protein expression (FIG. 12B, top panel). Similar effects of CD19 and Lyn knockdown on apoptosis were observed using flow cytometry (FIG. 12C).

Figure 12D:
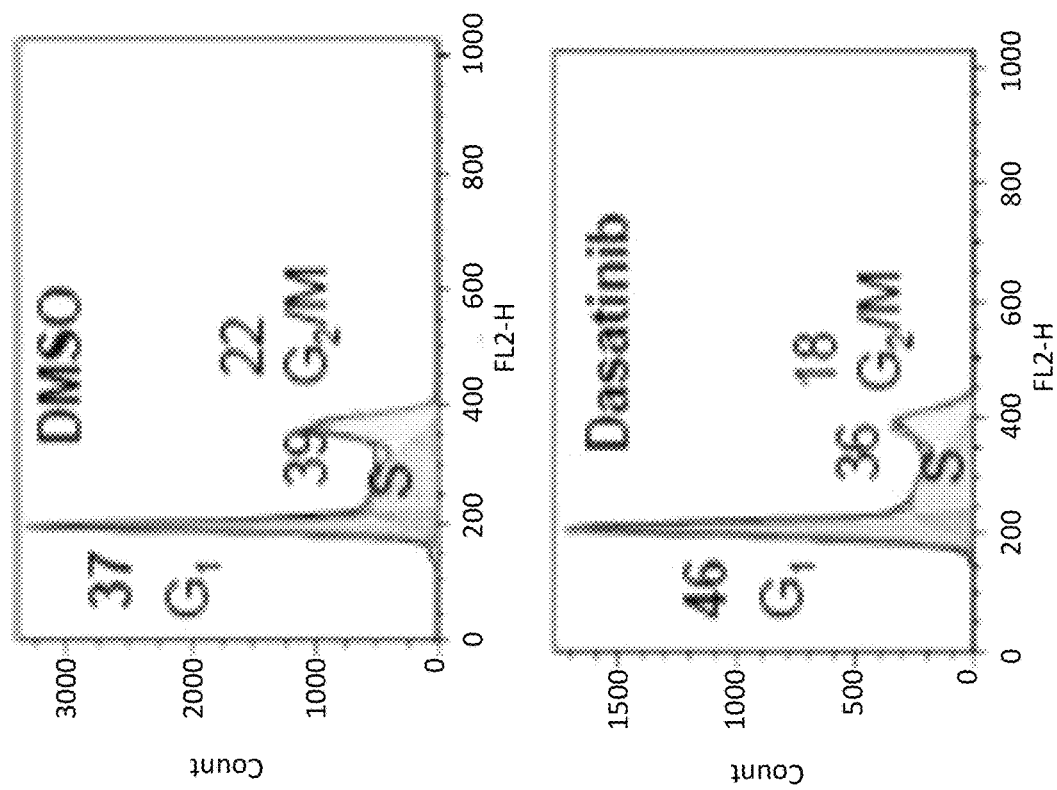
Figure 12D:
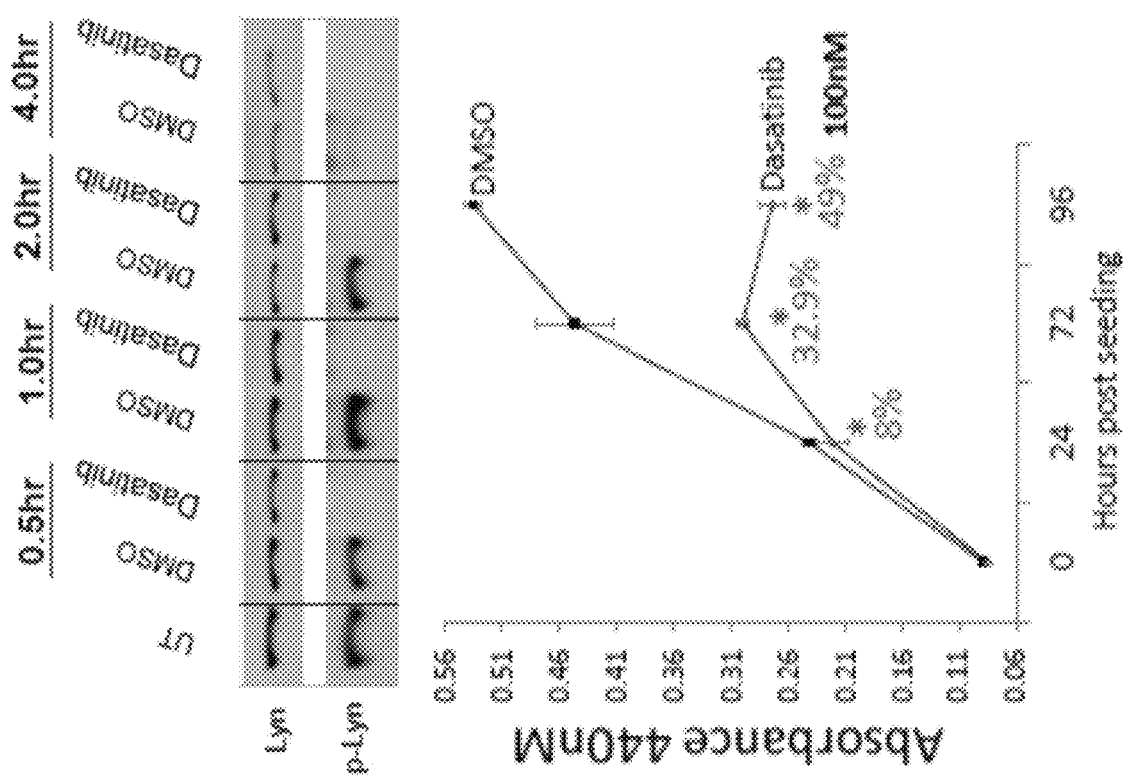

These novel findings demonstrate CD19-Lyn mediated signaling is important for the survival of B-ALL cells. This is significant because targeting the SFTK Lyn can be targeted for the treatment of B-ALL. For example, it is shown herein that the SFTK inhibitor Dasatinib (initially used to treat relapsed CML) is effective in inhibiting Lyn phosphorylation (FIG. 12D, top). It also impairs the growth of B-ALL cells via cell cycle arrest. (FIG. 12D, bottom).

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method of identifying a chemotherapeutic agent for the treatment of a B-cell neoplasm, said method comprising performing a binding assay between CD19 or a fragment thereof and phosphatidylinositide 3-kinase (PI3K) in the presence of at least one test compound,
   wherein a decrease in the amount of CD19-PI3K binding in the presence of the test compound compared to the binding in the absence of the test compound indicates that the compound is a chemotherapeutic agent for the treatment of a B-cell neoplasm,
   wherein said fragment of CD19 comprises the cytoplasmic tail of CD19, and
   wherein said CD19 or fragment thereof is human or murine and wherein said PI3K is human or murine.

2. The method of claim 1, wherein said binding assay is a cell-based screening assay.

3. The method of claim 1, wherein said CD19 or fragment thereof is the cytoplasmic tail of CD19.

4. The method of claim 1, wherein said test compound is a small molecule, peptide, or antibody.

5. The method of claim 1, wherein said B-cell neoplasm is a lymphoma or B-cell acute lymphoblastic leukemia.

6. The method of claim 1, wherein said binding assay is selected from the group consisting of yeast two hybrid assay, cell surface receptor binding assay, fluorescence energy transfer assay, liquid chromatography, membrane filtration assay, ligand binding assay, radiobinding assay, immunoprecipitation, radioimmunoassay, enzyme-linked immunosorbent assays (ELISA), immunohistochemical assays, Western blot, and surface plasmon resonance.

7. The method of claim 1, wherein said binding assay comprises immobilizing said CD19 or fragment thereof to a solid support and measuring the amount of PI3K bound to the immobilized CD19 in the presence of the test compound.

8. The method of claim 4, wherein said test compound is a peptide which is about 5 to about 50 amino acids in length, has at least 90% identity with CD19, and encompasses tyrosines 482 and/or 513 of CD19.

9. The method of claim 1, wherein said B-cell neoplasm is selected from the group consisting of lymphoma, non-Hodgkin's lymphoma, B-cell acute lymphoblastic leukemia, and chronic lymphocytic leukemia.

10. The method of claim 1, wherein said B-cell neoplasm is a B-cell lymphoma.

11. The method of claim 1, wherein said binding assay comprises immobilizing said PI3K to a solid support and measuring the amount of CD19 bound to the immobilized PI3K in the presence of the test compound.

* * * * *

UNITED STATES PATENT AND TRADEMARK OFFICE
CERTIFICATE OF CORRECTION

PATENT NO. : 10,983,109 B2
APPLICATION NO. : 14/397060
DATED : April 20, 2021
INVENTOR(S) : Thomas-Tikhonenko et al.

It is certified that error appears in the above-identified patent and that said Letters Patent is hereby corrected as shown below:

On the Title Page

Item (60), Related U.S. Application Data:
Please delete the year "2013" and insert therefor --2012--.

Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*